(12) United States Patent
Zhu et al.

(10) Patent No.: US 10,780,071 B2
(45) Date of Patent: *Sep. 22, 2020

(54) COMPOSITIONS, METHODS AND/OR DEVICES FOR PREVENTION AND/OR TREATMENT OF DRY EYE DISORDERS

(71) Applicant: Brien Holden Vision Institute Limited, Sydney, New South Wales (AU)

(72) Inventors: Hua Zhu, Bexley (AU); Judith Louise Flanagan, Newtown (AU)

(73) Assignee: Brien Holden Vision Institute Limited, Sydney, New South Wales (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/990,228

(22) Filed: May 25, 2018

(65) Prior Publication Data

US 2019/0022046 A1    Jan. 24, 2019

Related U.S. Application Data

(63) Continuation of application No. 14/414,030, filed as application No. PCT/AU2013/000759 on Jul. 9, 2013, now Pat. No. 10,004,714.

(30) Foreign Application Priority Data

Jul. 9, 2012 (AU) .................................. 2012902937

(51) Int. Cl.

| | | |
|---|---|---|
| A61K 31/20 | (2006.01) | |
| A61K 31/23 | (2006.01) | |
| A61K 31/202 | (2006.01) | |
| A61K 31/568 | (2006.01) | |
| A61K 9/00 | (2006.01) | |
| A61K 47/06 | (2006.01) | |
| A61K 47/14 | (2017.01) | |
| A61K 47/24 | (2006.01) | |
| A61K 45/06 | (2006.01) | |
| A61K 38/18 | (2006.01) | |
| A61K 47/44 | (2017.01) | |
| A61K 38/13 | (2006.01) | |
| A61K 31/5685 | (2006.01) | |
| A61K 31/7052 | (2006.01) | |
| A61L 12/12 | (2006.01) | |

(52) U.S. Cl.
CPC ............ *A61K 31/23* (2013.01); *A61K 9/0048* (2013.01); *A61K 31/20* (2013.01); *A61K 31/202* (2013.01); *A61K 31/568* (2013.01); *A61K 31/5685* (2013.01); *A61K 31/7052* (2013.01); *A61K 38/13* (2013.01); *A61K 38/1841* (2013.01); *A61K 45/06* (2013.01); *A61K 47/06* (2013.01); *A61K 47/24* (2013.01); *A61K 47/44* (2013.01); A61L 12/12 (2013.01)

(58) Field of Classification Search
CPC ...... A61K 31/20; A61K 31/23; A61K 31/202; A61K 31/568; A61K 31/5635; A61K 47/06; A61K 47/24; A61K 47/44; A61K 9/00; A61K 45/06
See application file for complete search history.

(56) References Cited

U.S. PATENT DOCUMENTS

| | | |
|---|---|---|
| 4,485,029 A | 11/1984 | Kato et al. |
| 4,866,049 A | 9/1989 | Maumenee |
| 2006/0029958 A1 | 2/2006 | Schlievert et al. |
| 2010/0016264 A1 | 1/2010 | Connor et al. |

FOREIGN PATENT DOCUMENTS

| | | |
|---|---|---|
| WO | WO 2002/083059 | 10/2002 |
| WO | WO 2008/057442 | 5/2008 |
| WO | WO 2008/137826 | 11/2008 |
| WO | WO 2010/089046 | 8/2010 |
| WO | WO 2011/157428 | 12/2011 |
| WO | WO 2012/068948 | 5/2012 |

OTHER PUBLICATIONS

Mayo Clinic, Jun. 3, 2011 (Treatment for dry Eyes Focuses on relieving Symptoms).*
International Search Report dated Aug. 12, 2013 for PCT/AU2013/000759.
McCabe, E and Narayanan, S. "Advancement in Anti-Inflammatory therapy for dry Eye Syndrome", Optometry, Oct. 2009, vol. 80, No. 10, pp. 555-566.
Sullivan, D.A., et al., "Androgens and Dry Eye in Sjogren's Syndrome", Annals New York Academy of Sciences, Jun. 1999, vol. 876, pp. 312-324.
Markweg-Hanke, M., et al. "Dodecanoic acid inhibition of a lipase from Acinetobacter sp. OPA 55", Enzyme and microbial Technology vol. 17, pp. 512-516, 1995.
Shine et al., "Association of Monoglyceride Nonpolar Lipids with Dry Eye Signs in Blepharitis Patients" IOVS, vol. 43, 2002.
The Ocular Surface, 2007 Report of the International Dry Eyes Workshop (DEWS), vol. 5, No. 2, Apr. 2007.
McCulley, James P, et al., Meibomian Gland Function and the Tear Lipid Layer, The Ocular Surface, vol. 1, No. 3, Jul. 1, 2003, pp. 97-106.
McCulley, James P, et al., The Lipid Layer of Tears: Dependent on Meibomian Gland Function, Experimental Eye Research, Academic Press Ltd, London, vol. 78, No. 3, Mar. 1, 2004, pp. 361-365.

(Continued)

Primary Examiner — Zohreh A Fay
(74) Attorney, Agent, or Firm — Jones Day

(57) ABSTRACT

The present disclosure relates to compositions, methods and devices for treating, reducing or preventing one or more eye disorders, particularly dry eye disorders, in a subject by administering an amount of one or more fatty acids and/or fatty acid esters therapeutically effective to inhibit lipase activity while permitting bacterial growth or without substantially altering the dynamic microbial community of the eye. Typically, the fatty acids and/or fatty acid esters are $C_8$ to $C_{16}$ fatty acids and/or fatty acid esters.

14 Claims, 11 Drawing Sheets

(56) References Cited

OTHER PUBLICATIONS

Ruiz, C., et al., Activation and Inhibition of Candida rugosa and Bacillus-related lapases by saturated fatty acids, evaluated by a new colorimetric microassay, Biochimica ET BioPhysica ACTA (BBA)—General Subjects, Elsevier, Amsterdam NL, vol. 1672, No. 3, Jun. 11, 2004, pp. 184-191.

Sun, C. Q., et al., Antibacterial actions of fatty acids and monoglycerides against Helicobacter pylori, Fems Immunology and Medial Microbiology, Elsevier Science B.V., Amsterdam, NL, vol. 36, No. 1-2, May 15, 2003, pp. 9-17.

Desbois, Andrew P., et al., Antibacterial free fatty acids: activities, mechanisms of action and biotechnological potential, Applied Microbiology and Biotechnology, Springer, Berlin, DE, vol. 85, No. 6, Dec. 3, 2009, pp. 1629-1642.

Arciniega, Juan C., et al., Effects of free fatty acids on Meibomian lipid films, Experimental Eye Research, Academic Press Ltd., London, vol. 93, No. 4, Jun. 10, 2011, pp. 452-459.

Schlievert, P. M., et al., Effect of Glycerol Monolaurate on Bacterial Growth and Toxin Production, Antimicrobial Agents and Chemotherapy, American Society for Microbiology, US, vol. 36, No. 3, Mar. 1, 1992, pp. 626-631.

Graham, Joanna E. et al., Ocular Pathogen or Commensal: A PCR-Based Study of Surface Bacterial Flora in Normal and Dry Eyes, Investigative Ophthalmology & Visual Science, vol. 48, No. 12, Dec. 1, 2007, pp. 5616-5623.

Ruzin, et al., Equivalence of Lauric Acid and Glycerol Monolaurate as Inhibitors of Signal Transduction in *Staphylococcus aureus*, Journal of Bacteriology, American Society for Microbiology, US, vol. 182, No. 9, May 1, 2000, pp. 2668-2671.

Flanigan, Judith Louise, et al., Glycerol Monolaurate Inhibits Lipase Production by Clinical Ocular Isolates Without Affecting Bacterial Cell Viability, Investigative Ophthalmology & Visual Science, vol. 57, No. 2, Feb. 12, 2016, pp. 544-550.

Mingsheng Luo et al. "Pharmaceutical Excipients ($2^{nd}$ Edition)", Sichuan Science and Technology Press, Jan. 2006, p. 882 (with English translation).

\* cited by examiner

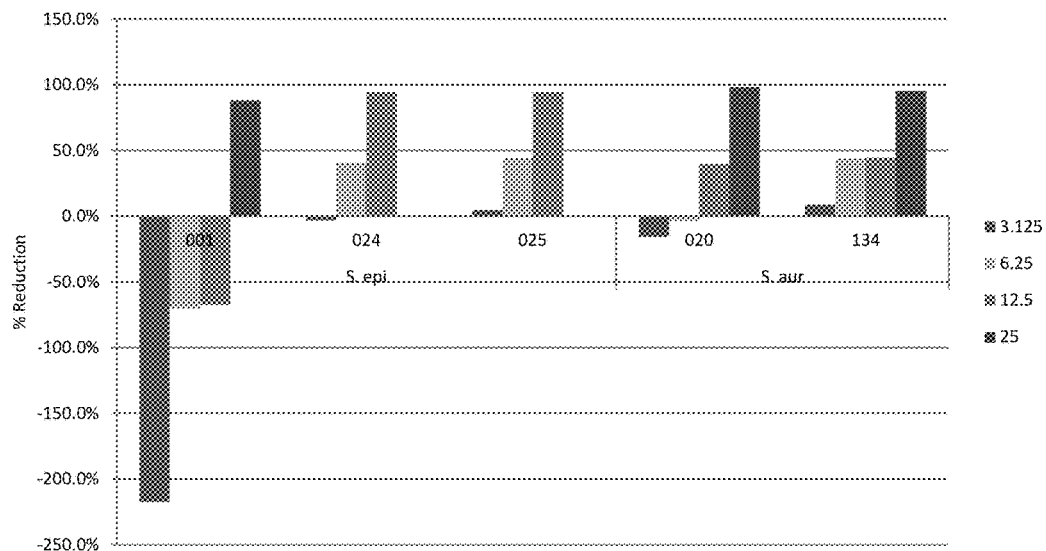
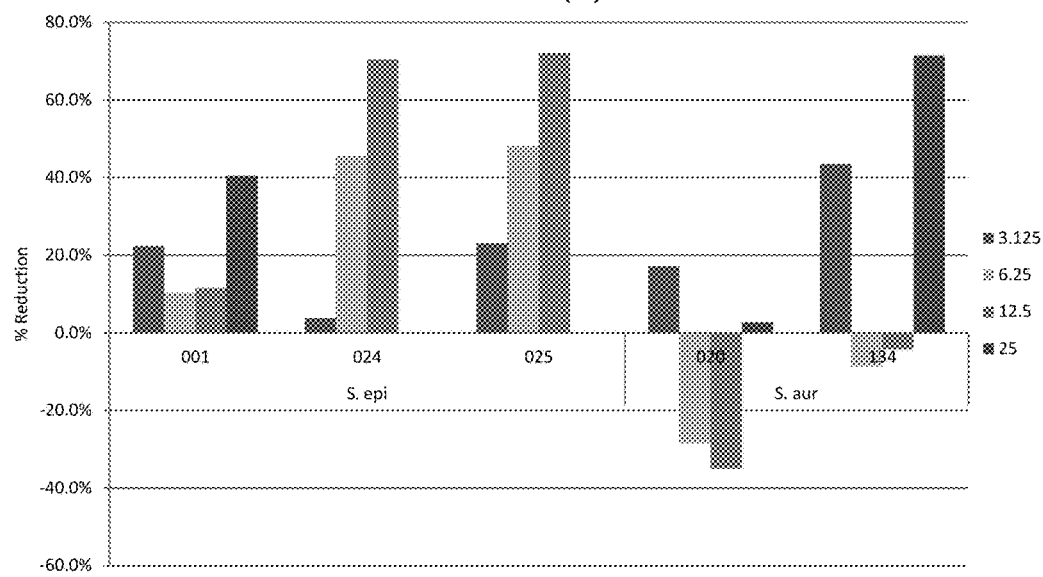

COMPOSITIONS, METHODS AND/OR DEVICES FOR PREVENTION AND/OR TREATMENT OF DRY EYE DISORDERS

CROSS-REFERENCE

This application is a continuation of U.S. patent application Ser. No. 14/414,030, filed Jan. 9, 2015, which is the National Phase application of International Application No. PCT/AU2013/000759, filed 9 Jul. 2013, which designates the United States and was published in English, which claims priority to AU 2012902937 filed 9 Jul. 2012. These applications, in their entirety, are incorporated herein by reference.

FIELD OF THE INVENTION

The Invention relates to compositions, methods and/or devices for reducing ocular discomfort associated with various diseases or conditions, in particular dry eye disorders. The invention also relates to the prevention and/or treating dry eye disorders, in particular the invention is directed to preventing or reducing symptoms associated with dry eye disorders, including when associated with contact lens wear. The present invention also relates to methods of treating, reducing or preventing such disorders or conditions using the disclosed compositions and devices.

BACKGROUND OF THE INVENTION

Dry eye is a disorder of the eye due to tear deficiency or excessive evaporation, which causes damage to the ocular surface and is associated with symptoms of ocular discomfort such as itchiness, irritation, foreign body sensation, redness, photophobia, pain and paradoxical tearing from corneal irritation. These symptoms are often worse toward the end of the day or after prolonged periods of time requiring vision attention such as reading, driving, or computer work. Tens of millions of people suffer from these debilitating symptoms.

The causes of dry eye disorders have been attributed to either decreased tear production (aqueous-deficient dry eye) for example, lacrimal gland disease, and/or excessive tear evaporation (evaporative dry eye) for example, arising from contact lens wear. Meibomian gland dysfunction (MGD) is considered to be a sign of dry eye disorders. Phenotypic changes within, or alteration of the dynamic composition of the ocular commensal bacteria such as coagulase-negative staphylococci, *Staphylococcus aureus* and *Propionibacterium acnes* may create an imbalance and may trigger release of bacterial virulence factors such as endotoxins, lipopolysaccharides, and/or lipase causing eyelid inflammation, degradation of lipids secreted by meibomian glands, and directly influencing tear film stability and favouring tear evaporation. The greatest bacterial lipolytic activity was found in the patients with MGD. Commonly used dry eye treatments increase humidity of the ocular surface and improve symptoms by use of lubricants/artificial tears and/or topically applied anti-inflammatory medication such as cyclosporine A or corticosteroids. Oral antibiotics such as tetracycline and its derivatives have also been used in management of some types of MGD. However, these available treatments do not represent a cure and excessive antibiotic use is known to be problematic given the tendency for subjects to develop antibiotic resistance. Thus, there is a need to develop novel and better dry eye therapies.

US 2010/0016264 describes compositions and methods for treating eye conditions, specifically dry eye, with progestagen with or without testosterone. For example, a composition is described which includes 15% progesterone in Vanicream®. U.S. Pat. No. 4,485,029 describes the use of glycerol monolaurate in combination with one or more other anti-microbial agents for cleaning, disinfecting or preserving contact lenses. The glycerol monolaurate is used at concentrations which seem to exhibit anti-microbial, or at least bacteriostatic, properties and were not applied directly to the eye. U.S. Pat. No. 5,472,703 describes an ophthalmic lens that claims to lessen the risk of bacterial infection in the cornea. The lens has impregnated in it, or coated on the surface, an ester of polyhydric aliphatic alcohol and a fatty acid.

Dry eye disorders and ocular discomfort associated with dry eye disorders are still a substantial problem. The present invention is directed to overcoming and/or ameliorating at least one of the disadvantages of the prior art as will become apparent from the discussion herein.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The subject invention comprises the surprising effect that $C_8$ to $C_{16}$ fatty acids and/or $C_8$ to $C_{16}$ fatty acid esters, for example, glycerol monolaurate and/or lauric acid, may act as bacterial lipase inhibitors. The inventors have surprisingly found that when $C_8$ to $C_{16}$ fatty acids and/or fatty acid esters are included in preparations applied to the eye, lipase activity may be inhibited which results in increased tear film stability and/or improved quality of tear lipids. The increased tear film stability and/or improved quality of tear lipids may be determined as increased tear break up time (also referred to as tear BUT). Inhibition of lipase activity may be by, for example, inhibition of lipase production by bacteria. A further surprising effect is the ability of the $C_8$ to $C_{16}$ fatty acids and/or fatty acid esters to inhibit lipase activity while permitting bacterial growth (ie without antibacterial activity), especially of commensal bacteria of the human eye. Alternatively, the $C_8$ to $C_{16}$ fatty acids and/or fatty acid esters inhibit lipase activity without substantially altering the dynamic microbial community of the eye (this is explained further below). The present invention is directed, in one aspect, to the use of one or more $C_8$ to $C_{16}$ fatty acids and/or fatty acid esters to inhibit lipase activity without substantially altering the growth, viability, numbers and/or types of commensal bacteria of the eye. In certain embodiments, compositions comprising $C_8$ to $C_{16}$ fatty acids and/or fatty acid esters may be used to inhibit lipase activity without substantially altering the dynamic microbial community of the eye, wherein the composition has minimal or insubstantial antibacterial activity, for example, on the commensal bacteria of the eye. In certain embodiments, compositions comprising $C_8$ to $C_{16}$ fatty acids and/or fatty acid esters may be used to inhibit lipase activity without substantially altering the dynamic microbial community of the eye, wherein the composition has no antibacterial activity, for example, with respect to commensal bacteria of the eye. Certain embodiments are directed to a therapeutic treatment for a dry eye disorder using $C_8$ to $C_{16}$ fatty acids and/or fatty acid esters, for example, glycerol monolaurate and/or lauric acid, as lipase inhibitors. The fatty acids and/or fatty acid esters suitable for use in a composition, method or use of the invention are one or more of the following: $C_8$ to $C_{16}$ fatty acids and/or fatty acid esters. $C_8$ to $C_{14}$ fatty acids and/or $C_8$ to $C_{14}$ fatty acid esters, $C_8$ fatty acids and/or $C_8$ fatty acid esters, $C_{10}$ fatty acids and/or $C_{10}$ fatty acid esters, $C_{12}$ fatty acids and/or $C_{12}$ fatty acid esters, glycerol monolaurate, lauric acid capric acid, caprylic acid, myristic acid or a combination thereof.

The present invention relates to methods of treating and/or preventing an eye disorder in a subject by administering an amount of one or more $C_8$ to $C_{16}$ fatty acids and/or fatty acid esters therapeutically effective to inhibit lipase activity while permitting bacterial growth, especially of commensal bacteria of the human eye. The present invention relates to methods of treating and/or preventing an eye disorder in a subject by administering an amount of one or more $C_8$ to $C_{16}$ fatty acids and/or fatty acid esters therapeutically effective to inhibit lipase activity without substantially altering the dynamic microbial community of the eye. Preferably, the eye disorder is a dry eye disorder. The fatty acids and/or fatty acids ester may be any one or more of the following: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid, capric acid, caprylic acid, myristic acid or a combination thereof. Preferably, the fatty acid ester is glycerol monolaurate. Preferably, the fatty acid is lauric acid. In certain embodiments, the composition may contain glycerol monolaurate and lauric acid. In certain embodiments, the fatty acid is capric acid.

The present invention relates to a method of treating or preventing an eye disorder in a subject comprising administering an amount of glycerol monolaurate or lauric acid therapeutically effective to inhibit lipase activity while permitting bacterial growth of commensal bacteria of the eye.

The present invention also relates to methods of treating and/or preventing a dry eye disorder in a subject by administering an amount of one or more $C_8$ to $C_{14}$ fatty acids and/or fatty acid esters therapeutically effective to inhibit lipase activity while permitting bacterial growth of commensal bacteria of the human eye.

The present invention also relates to methods of treating and/or preventing a dry eye disorder in a subject by administering an amount of one or more $C_8$ to $C_{14}$ fatty acids and/or fatty acid esters therapeutically effective to inhibit lipase activity without substantially altering the dynamic commensal bacterial community associated with the eye. Typically, the amount of one or more $C_8$ to $C_{14}$ fatty acids and/or fatty acid esters used has minimal or insubstantial antibacterial activity.

The present invention also relates to methods of treating and/or preventing a dry eye disorder in a subject by administering an amount of glycerol monolaurate, lauric acid, capric acid, caprylic acid or combinations thereof therapeutically effective to inhibit lipase activity without substantially altering the dynamic commensal bacteria community associated with the eye. Typically, the amount of glycerol monolaurate, lauric acid, capric acid, caprylic acid or combinations thereof used has minimal or insubstantial antibacterial activity. The present invention includes both reducing the risk of development of these disorders by inhibiting or preventing their initial development, treating those disorders once diagnosed or combinations thereof.

One advantage of certain embodiments is the reduction of bacterial virulence factors such as lipase, without substantially altering commensal bacteria balance and/or substantially developing antibiotic resistance in target organisms.

Another advantage is that the $C_8$ to $C_{16}$ fatty acids and/or fatty acid esters may be used in a contact lens care solution and/or directly (or indirectly) applied to the contact lens so as to be administered to the eye via the contact lens when fitted or combinations thereof. The $C_8$ to $C_{16}$ fatty acids and/or fatty acid esters may then be slowly desorbed or otherwise released from the contact lens into the relevant area, for example, the upper tarsal conjunctiva of the upper eyelid or lid margins whilst the contact lens is fitted to the eye. This means that the $C_8$ to $C_{16}$ fatty acids and/or fatty acid esters may be less likely to be drained away by tears than in other modes of administration. This advantage is also applicable to one or more of the following fatty acids and/or fatty acids ester: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid capric acid, caprylic acid, myristic acid or a combination thereof.

Without intending to be bound by any theory or mode of action, it is believed that when $C_8$ to $C_{16}$ fatty acids and/or fatty acid esters are administered to the subject they may inhibit lipase activity by, for example, inhibiting the production of lipase by bacteria associated with the eye. This may then reduce the breakdown of lipids, such as the meibum produced by the meibomian gland, so that the lipids may perform their function of limiting evaporation and stabilising the tear film. The inhibition of lipase activity may also reduce the amount of irritating lipid breakdown products.

In certain embodiments, the lipase activity is bacterial lipase activity. In certain embodiments, the $C_8$ to $C_{16}$ fatty acids and/or fatty acid esters inhibit lipase activity, for example, bacterial lipases. In certain embodiments, the $C_8$ to $C_{16}$ fatty acids and/or fatty acid esters inhibit lipase activity by inhibiting production of lipases, for example, bacterial lipases. In certain embodiments, lipase activity is inhibited by 30 to 80%, or any one of the following ranges: 40 to 80%, 60% to 80%, 45 to 75%, 40 to 50%, 50 to 70%, 55 to 80%, 30% to 45% or 35 to 50%. Where the fatty acid is lauric acid, lipase activity is inhibited by any one of the following ranges: 40 to 72%, 40 to 48%, 40 to 50%, 50 to 70%, 55 to 75% or 35 to 75%. Where the fatty acid ester is glycerol monolaurate, lipase activity is inhibited by any one of the following ranges: 46 to 72%, 0.70 to 75%, 45 to 55%, 46 to 70%, 55 to 72%, 60 to 75% or 85 to 80%. Where the fatty acid is lauric acid and fatty acid ester is glycerol monolaurate, the lipase activity is inhibited by any one of the following ranges: 40 to 72%, 70 to 75%, 40 to 50%, 50 to 70%, 55 to 80% or 35 to 75%. The % inhibitions are when assayed as described in Example 1.

The invention also relates to a method of treating or preventing an eye disorder in a subject by administering an amount of one or more $C_8$ to $C_{16}$ fatty acids and/or fatty acid esters therapeutically effective to inhibit lipase production while permitting bacterial growth (ie without having antibacterial activity). Typically, the amount of one or more $C_8$ to $C_{16}$ fatty acids and/or fatty acid esters inhibits lipase activity without substantially altering the dynamic microbial community of the eye. Preferably, the eye disorder is a dry eye disorder. In one embodiment, there is a method of treating or preventing a dry eye disorder in a subject comprising administering an amount of one or more $C_8$ to $C_{16}$ fatty acids and/or fatty acid esters therapeutically effective to inhibit lipase production without substantially altering the dynamic microbial community of the eye, wherein the amount used has minimal or insubstantial antibacterial activity. In another embodiment, there is a method of treating or preventing a dry eye disorder in a subject comprising administering an amount of one or more $C_8$ to $C_{16}$ fatty acids and/or fatty acid esters therapeutically effective to inhibit lipase production without substantially altering the dynamic microbial community of the eye, wherein the amount used has no antibacterial activity. In another embodiment, there is a method of treating or preventing a dry eye disorder in a subject comprising administering one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof. In an amount therapeutically effective to inhibit lipase production without substantially altering the dynamic microbial community of the eye, wherein the amount used has minimal or insubstantial antibacterial activity. In another embodiment, there is a method of treating or preventing a dry eye disorder in a subject comprising administering one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase production without substantially altering the dynamic microbial community of the eye, wherein the amount used has no antibacterial activity.

The invention also relates to a method of alleviating dry eye symptoms in a subject comprising administering an amount of one or more $C_8$ to $C_{16}$ fatty acids and/or fatty acid esters therapeutically effective to inhibit lipase activity while permitting bacterial growth (ie without having antibacterial activity). Alternatively, the method comprises administering an amount of one or more $C_8$ to $C_{16}$ fatty acids and/or fatty acid esters therapeutically effective to inhibit lipase activity without substantially altering the dynamic microbial community of the eye. In one embodiment, there is a method of alleviating dry eye symptoms in a subject comprising administering an amount of one or more $C_8$ to $C_{16}$ fatty acids and/or fatty acid esters therapeutically effective to inhibit lipase production without substantially altering the dynamic microbial community of the eye, wherein the amount used has minimal or insubstantial antibacterial activity. In one embodiment, there is a method of alleviating dry eye symptoms in a subject comprise administering an amount of one or more $C_8$ to $C_{16}$ fatty acids and/or fatty acid esters therapeutically effective to inhibit lipase activity without substantially altering the dynamic microbial community of the eye, wherein the amount used has no antibacterial activity.

The present invention relates to a method of alleviating dry eye symptoms in a subject comprising administering one or more of the following fatty acids/and fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase production while permitting bacterial growth. In one embodiment, there is a method of alleviating dry eye symptoms in a subject comprising administering one or more of the following fatty acids/and fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase production without substantially altering the dynamic microbial community of the eye, wherein the amount used has minimal or insubstantial antibacterial activity. In another embodiment, there is a method of alleviating dry eye symptoms in a subject comprising administering one or more of the following fatty acids/and fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase production without substantially altering the dynamic microbial community of the eye, wherein the amount used has no antibacterial activity. The lipase activity may be inhibited by inhibiting lipase production.

Certain embodiments are directed to the use of one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof in combination with androgen or an androgen analogue to synergistically enhance treatment and/or prevention of dry eye disorder when compared to use of these agents alone. Certain embodiments are directed to the use of androgen or an androgen analogue in combination with glycerol monolaurate and/or lauric acid to synergistically enhance treatment and/or prevention of a dry eye disorder when compared to use of these agents alone. Without intending to be bound by any theory or mode of action, one likely mechanism of action of androgen or an androgen analogue includes promoting glandular function in lacrimal/meibomian glands and consequently improving quantity (and quality) of tear and meibum secretion. Further information on the use of androgens in the treatment of eye disease is found in U.S. Pat. No. 5,620,921 which describes the topical application to the eye of a therapeutic amount of androgen, androgen analogue or TGF-□ for the treatment of keratoconjunctivitis sicca (KCS) (ie dry eye syndrome). U.S. Pat. No. 5,620,921 is incorporated by reference in its entirety.

Accordingly, the methods of the present invention may further comprise administration of a therapeutically effective amount of androgen or androgen analogue and/or a therapeutically effective amount of an anti-inflammatory agent. For example, the androgen or androgen analogue is preferably one or more of the following: dehydroepiandrosterone (DHEA), androsterone, testosterone and dihydrotestosterone (DHT). The anti-inflammatory agent may be one or more of the following: azithromycin, cyclosporine A, omega-3 fatty acids, and transforming growth factor beta (TGF-β).

In a preferred embodiment, a method of the invention is for the treatment and/or prevention of dry eye disorders including one or more of the following: aqueous-deficient dry eye and evaporative dry eye. The methods of the invention may also be useful for the treatment and/or prevention of dry eye disorders caused by one or more of the following: the wearing of the ophthalmic device such as a contact lens, Sjögren's syndrome, an autoimmune disorder, non-Sjögren aqueous-deficient dry eye disorder resulting from lacrimal gland insufficiency, lacrimal duct obstruction, meibomian gland disease, blepharitis, eyelid aperture disorders, conjunctival disorders and/blink disorders.

In certain embodiments, the concentration of $C_8$ to $C_{16}$ fatty acids and/or related fatty acid esters in solutions is about 0.1 to 50 μg/ml. Preferably, the concentration is about 1 to about 25 μg/ml, about 2.5 to about 25 μg/ml, 2.5 to about 15 μg/ml, or about 2.5 to about 10 μg/ml. In other embodiments, the concentration is about 5 to less than 25 μg/ml. Alternatively, the concentration is 12.5 to less than 25 μg/ml. Alternatively, the concentration is 12.5 to 22.5 μg/ml. Alternatively, the concentration is about 12.5 to about 20 μg/ml. Alternatively, the concentration is about 12.5 to 17.5 μg/ml. Alternatively, the concentration is 12.5 to 15 μg/ml. Alternatively, the concentration is 15 to 22.5 μg/ml. Alternatively, the concentration is about 15 to about 20 μg/ml. Alternatively, the concentration is 15 to 17.5 µg/ml. Alternatively, the concentration is 17.5 to 20 µg/ml. Alternatively, the concentration is 17.5 to less than 25 µg/ml. Alternatively, the concentration of about 20 to less than 25 µg/ml. Alternatively, the concentration is 12.5 to 50 µg/ml. Alternatively, the concentration is 25 to 50 µg/ml. These concentrations are also applicable to one or more of the following fatty acids and/or fatty acids ester: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid capric acid, caprylic acid, myristic acid or a combination thereof. Preferably, the fatty acid and/or fatty acid ester is in any composition of the invention in an amount sufficient to achieve a tear film concentration of about 5 to 50 µg/ml, preferably 10 g/ml.

In certain embodiments, the amount of $C_8$ to $C_{16}$ fatty acids and/or related fatty acid esters in solutions is about 0.001% to about 0.050% by weight of the total volume of the solution. Typically, the concentration is about 0.001% to 0.025%, about 0.0025% to 0.025%, about 0.0025% to 0.01%, 0.0025% to 0.015%, about 0.005% to less than 0.025%, about 0.0125% to less than 0.025%, about 0.0125% to 0.0225%, about 0.0125% to 0.02%, about 0.0125% to 0.0175%, about 0.0125% to 0.015%, about 0.015% to 0.0225%, about 0.015% to 0.02%, about 0.15% to 0.0175%, about 0.0175% to 0.02%, about 0.0175% to less than 0.025%, about 0.02 to less than 0.025, about 0.0125% to 0.05%, or about 0.025% to 0.05% by weight of the total volume of the solution. These concentrations are also applicable to one or more of the following fatty acids and/or fatty acids ester: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid capric acid, caprylic acid, myristic acid or a combination thereof.

In certain embodiments, the amount of $C_8$ to $C_{16}$ fatty acids and/or related fatty acid esters in viscous formulations such as gels, ointments and creams is about 0.0001% to 0.1% by weight of the total weight of the formulation. Typically, the concentration is about 0.005% to 0.05% by weight of the total weight of the formulation. In other aspects, the concentration is about 0.005% to 0.01% by weight of the total weight of the formulation. In other aspects, the concentration is about 0.05% to 0.5% by weight of the total weight of the formulation. In other aspects, the concentration is about 0.01% to 0.95% by weight of the total weight of the formulation. In other aspects, the concentration is about 0.1% to 1% by weight of the total weight of the formulation. Alternatively, the concentration is about 0.025% to less than 0.1% by weight of the total weight of the formulation. These concentrations are also applicable to one or more of the following fatty acids and/or fatty acids ester: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid capric acid, caprylic acid, myristic acid or a combination thereof.

In certain embodiments, the androgen or androgen analogue comprises about 0.0001 to about 5% by weight of the total weight of the composition administered. In other embodiments, the androgen or androgen analogue comprises about 0.05% to about 3% by weight of the total weight of the composition. In other embodiments, the androgen or androgen analogue comprises about 0.001% to about 0.03% by weight of the total weight of the composition. In certain embodiments, the androgen or androgen analogue comprises about 0.02% by weight of the total weight of the composition.

In certain embodiments, the anti-inflammatory agent comprises about 0.001% to about 5% by weight of the total weight of the composition administered. In certain embodiments, the anti-inflammatory agent comprises about 0.001% to about 1% by weight of the total weight of the composition. In certain embodiments, the anti-inflammatory agent comprises about 0.2%. In certain embodiments, the anti-inflammatory agent comprises about 1% to 2% by weight of the total weight of the composition.

In certain embodiments, the $C_8$ to $C_{16}$ fatty acids and/or fatty acid esters are administered in the form of eye drops. In certain embodiments, the $C_8$ to $C_{16}$ fatty acids and/or related fatty acid esters are administered in the form of an eye ointment or gel. In other embodiments, the $C_8$ to $C_{16}$ fatty acids and/or related fatty acid esters are administered in the form of a cream on and around the lid margins. In certain embodiments, the $C_8$ to $C_{16}$ fatty acids and/or related fatty acid esters are administered orally. Alternatively, the $C_8$ to $C_{16}$ fatty acids and/dr related fatty acid esters are released (for example, diffused) from an ophthalmic device such as a contact lens. The $C_8$ to $C_{16}$ fatty acids or fatty acid esters may be in composition with or separate from the androgen or androgen analogue and/or anti-inflammatory agent. The $C_8$ to $C_{16}$ fatty acids and/or related fatty acid esters may be administered concurrently or non-concurrently with the androgen or androgen analogue and/or anti-inflammatory agent. Where there is both an androgen or androgen analogue and/or an anti-inflammatory agent, these may be in the same composition or separate and administered either concurrently or non-concurrently.

In certain embodiments, the subject is first assessed as needing treatment for dry eye disorder, likely to need treatment for a dry eye disorder, being at risk of developing a dry eye disorder, or being at particular risk (e.g. from complications or consequence of developing the condition) if a dry eye disorder is developed, such that preventing or inhibiting the development of dry eye disorder or treatment of the dry eye disorder was considered necessary.

In any of the methods of the invention, the $C_8$ to $C_{16}$ fatty acids and/or fatty acid esters, androgen, androgen analogue and/or anti-inflammatory agents may be administered in the form of the compositions disclosed herein. The fatty acids and/or fatty acid esters, androgen, and/or anti-inflammatory agents may be administered in the form of the compositions disclosed herein, wherein one or more of the following fatty acids and/or fatty acids ester are in the composition: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid capric acid, caprylic acid, myristic acid or a combination thereof. Alternatively, administration may be from a contact lens as described elsewhere in the specification.

In another aspect the present invention provides a contact lens comprising a therapeutically effective amount of one or more of the following: $C_8$ to $C_{16}$ fatty acids and/or fatty acid esters, and optionally an androgen or androgen analogue and/or anti-inflammatory agent. Certain embodiments provide a contact lens comprising a therapeutically effective amount of $C_8$ to $C_{16}$ fatty acids and/or fatty acid esters, an androgen or androgen analogue and anti-inflammatory agent. Certain embodiments provide a contact lens comprising one or more of the following: an amount of one or more $C_8$ to $C_{16}$ fatty acids and/or related fatty acid esters, antiinflammatory agent and optionally an androgen or androgen analogue. Certain embodiments provide a contact lens comprising: $C_8$ to $C_{16}$ fatty acids and/or fatty acid esters, an androgen or androgen analogue, and anti-inflammatory agent. The actives may be loaded onto the contact lens by one or more of the following: drug loading existing lenses; using a barrier such as Vitamin E; manufacturing the lens with the actives at least substantially entrapped inside; and using techniques such as molecular imprinting, particle-laden soft contact lenses or supercritical solvent impregnations etc. The actives may be released from the contact lens during wear by diffusion and/or other methods.

In another aspect, the present invention provides a composition suitable for administration to the eye comprising a therapeutically effective amount of one or more $C_8$ to $C_{16}$ fatty acids or fatty acid esters for the prevention and/or treatment of an eye disorder, preferably dry eye. The $C_8$ to $C_{16}$ fatty acids or fatty acid esters are therapeutically effective to inhibit lipase activity without having an anti-bacterial effect (ie bacterial growth is permitted so the commensal bacterial population remains unchanged). The composition may further comprise a therapeutically effective amount of androgen or androgen analogue and/or an anti-inflammatory agent. The preferred $C_8$ to $C_{16}$ fatty acids and/or fatty acid esters, androgens, androgen analogues and anti-inflammatory agents are disclosed herein. The androgen, androgen analogue and the anti-inflammatory agent may be in a different composition to the $C_8$ to $C_{16}$ fatty acids and/or fatty acid. The composition may be used to treat, reduce or prevent any of the forms of dry eye discussed herein.

In certain applications, the composition may be in a form suitable for topical administration to the eye in one or more of the following: an ointment, gel, spray, insert, eye drop and by release (for example diffusion) from a contact lens that is fitted to the eye. In certain embodiments, the composition is an aqueous composition, which is isotonic or substantially isotonic. In certain applications, the composition may also be formulated for topical or oral administration.

The present invention also relates to a pharmaceutical composition comprising an amount of one or more $C_8$ to $C_{16}$ fatty acids and/or fatty acid esters therapeutically effective to inhibit lipase activity while permitting bacterial growth and a pharmaceutically acceptable excipient, diluent or carrier. Typically, the pharmaceutical composition includes an androgen or androgen analogue and/or an anti-inflammatory agent as described herein.

In certain embodiments, the composition may be a contact lens care solution formulated so as to permit the lens to absorb and/or adsorb the $C_8$ to $C_{16}$ fatty acids and/or fatty acid esters, androgen or androgen analogue, and an anti-inflammatory agent from the solution so that the active(s) are either coated on the surface of the lens or absorbed-into the matrix of material of the lens or both and then released into the eye during wear. In another embodiment, the solution is an aqueous solution, which is isotonic or substantially isotonic.

The invention also relates to two or more compositions wherein one composition comprises one or more of the fatty acids and/or fatty acid esters disclosed herein and the second composition comprises the androgen or androgen analogue and/or an anti-inflammatory agent. Alternatively, the androgen or androgen analogue may be in a different composition to the anti-inflammatory agent.

In certain embodiments, the compositions described herein may further include one or more preservatives. Suitable preservatives include one or more of the following: benzalkonium chloride, chlorhexidine, chlorobutanol, polymyxin B sulphate, sorbic acid and Purite®. Further suitable preservatives are listed in the detailed description. Such preservatives typically would not be considered by a person skilled in the art as an active component of the composition suitable for the prevention or treatment of dry eye. In an alternative embodiments, the compositions may not include a preservative, ie, are preservative-free.

The compositions of the invention may further comprise one or more of the following: buffering agents, osmotic agents, surfactants, wetting agents, anti-oxidants, comfort enhancing agents, and osmoprotectants. For example, one or more comfort enhancing and/or wetting agent may be selected from the group comprising: cellulose derivatives such as hydroxypropyl methyl cellulose, carboxymethyl cellulose, methyl cellulose, hydroxyethyl cellulose, dextran, gelatin, polyols, liquids such as glycerin, polyethylene glycol, polyethylene glycol, polysorbate, propylene glycol, polyvinyl alcohol, povidone (polyvinyl pyrrolidone) and/or copolymers such as EO/PO block copolymers. In addition, compositions of the invention may include oil-in-water ophthalmic emulsions as carriers for the one or more of the fatty acids and/or fatty acid esters disclosed herein and/or androgen or androgen analogue.

The invention also relates to a composition that consists essentially of one or more of the following: $C_8$ to $C_{16}$ fatty acids and/or fatty acid esters and optionally androgen or androgen analogue and/or an anti-inflammatory agent. Certain embodiments relate to compositions that consist essentially of: $C_8$ to $C_{16}$ fatty acids and/or fatty acid esters, androgen or androgen analogue, and an anti-inflammatory agent. Typically, the fatty acids and/or fatty acids ester are one or more of the following: $C_8$ to $C_{14}$ fatty acids and/or fatty acid esters, $C_8$ fatty acids and/or fatty acid esters, $C_{10}$ fatty acids and/or fatty acid esters, $C_{12}$ fatty acids and/or fatty acid esters, glycerol monolaurate, lauric acid, capric acid, caprylic acid, myristic acid or a combination thereof, and wherein the compositions inhibit lipase activity without substantially altering the dynamic microbial community of the eye. Typically, the compositions inhibit lipase activity without substantially altering the growth, viability, numbers and/or types of commensal bacteria of the eye. In this specification "consists essentially of" means that the composition or contact lens care solution according to the invention does not contain any additional active pharmaceutical ingredients but may optionally include other non-active components such as salts and buffers in aqueous solution.

In certain embodiments, the composition consists of one or more of the following: $C_8$ to $C_{16}$ fatty acids and/or fatty acid esters and optionally androgen or androgen analogue and an anti-inflammatory agent, water and optionally salt and/or buffer, wherein the tonicity and/or pH of the composition is isotonic and within a physiologically acceptable range. In a further embodiment, the composition is an eye drop solution including glycerol monolaurate and the androgen dehydroepiandrosterone (DHEA) wherein the carrier comprises the fat-soluble ingredient carrier caprylic capric triglyceride, the non-ionic surfactant/emulsifier sorbitan monooleate, and the preservative chlorobutanol. Preferably the glycerol monolaurate is 0.001-0.05% of the eye drop. Preferably, the DHEA is 1-5% of the eye drop solution. In certain embodiments, the composition comprises: $C_8$ to $C_{16}$ fatty acids and/or fatty acid esters, androgen or androgen analogue, an anti-inflammatory agent, water and optionally salt and/or buffer, wherein the tonicity and pH of the composition is isotonic and within a physiologically acceptable range.

The present invention also provides a composition for use in the prevention, reduction and/or treatment of dry eye, as described in any of the embodiments of the invention.

Alternatively, the compositions disclosed herein may be administered to a subject first assessed as needing treatment for dry eye, likely to need treatment for dry eye, being at risk of developing dry eye, and/or being at particular risk (e.g. from complications or consequence of developing the condition) if dry eye is developed, such that preventing, reducing or inhibiting the development of dry eye was considered necessary.

In another aspect the present invention provides use of a therapeutically effective amount of one or more $C_8$ to $C_{16}$ fatty acids and/or fatty acid esters in the prevention and/or treatment of an eye disorder, preferably dry eye, in a subject. Alternatively, the present invention provides use of a therapeutically effective amount of one or more $C_8$ to $C_{16}$ fatty acids and/or fatty acid esters to, alleviate dry eye symptoms in a subject. The $C_8$ to $C_{16}$ fatty acids and/or fatty acid esters are therapeutically effective to inhibit lipase activity while permitting bacterial growth (ie without having anti-bacterial effect so that the commensal bacterial population remains unchanged). Preferably, the $C_8$ to $C_{16}$ fatty acids and/or fatty acid esters are therapeutically effective to inhibit lipase activity without substantially altering the dynamic microbial community of the eye wherein the amount used has minimal or insubstantial antibacterial activity. Preferably, the $C_8$ to $C_{16}$ fatty acids and/or fatty acid esters are therapeutically effective to inhibit lipase activity without substantially altering the dynamic microbial community of the eye, wherein the amount used has no antibacterial activity. Certain embodiments provide use of a therapeutically effective amount of one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof in the prevention and/or treatment of a dry eye disorder, in a subject. Certain embodiments provide use of a therapeutically effective amount of one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof to alleviate dry eye symptoms in a subject. Some embodiments may further comprise use of a therapeutically effective amount of androgen or androgen analogue and/or a therapeutically effective amount of an anti-inflammatory agent. Preferably, the subject is first assessed as needing treatment for dry eye, likely to need treatment for dry eye, being at risk of developing dry eye, or being, at particular risk (e.g. from complications or consequence of developing the condition) if dry eye is developed, such that preventing or inhibiting the development of dry eye was considered necessary. In another aspect, $C_8$ to $C_{16}$ fatty acids and/or fatty acid esters and androgen and anti-inflammatory agent are administered in the form of a pharmaceutical composition in a form suitable for administration to the eye. Exemplary fatty acids and/or fatty acid esters, androgens, and anti-inflammatory agents are disclosed herein. The composition may be used to treat, prevent or alleviate the symptoms of the forms of dry eye disorder disclosed herein.

In yet another aspect the present invention provides an ophthalmic device, wherein the device permits a therapeutically effective amount of one or more $C_8$ to $C_{16}$ fatty acids and/or fatty acid esters to be released (e.g. desorbed, diffused) from the device into the eye during wear by a subject. The device may also permit a therapeutically effective amount of androgen or androgen analogue and/or an anti-inflammatory agent to be released. The active agents released from the ophthalmic device are therapeutically effective to inhibit lipase activity without having an antibacterial effect (i.e. the commensal bacterial population remains unchanged) or with minimal or insubstantial antibacterial activity. In certain aspects, the active agents released from the ophthalmic device are therapeutically effective to inhibit lipase activity with no antibacterial activity. The device is used in the prevention or treatment of an eye disorder, preferably dry eye. Exemplary, $C_8$ to $C_{16}$ fatty acids and/or fatty acid esters, androgens, analogues of androgen and anti-inflammatory agents are disclosed herein. The ophthalmic device may treat, prevent or alleviate the symptoms of one or more of the forms of dry eye discussed herein. The subject may first be assessed as needing treatment for dry eye, likely to need treatment for dry eye, being at risk of developing dry eye, or being at particular risk if dry eye is developed as described herein. The ophthalmic device may be an ocular insert or punctal plug or a contact lens.

In another aspect the present invention provides a method of making an ophthalmic device as described herein, comprising the step of contacting an ophthalmic device with a solution comprising one or more $C_8$ to $C_{16}$ fatty acids and/or fatty acid esters and then applying the device to the eye. The device may also be contacted with androgen or androgen analogue and/or an anti-inflammatory agent. Where there is more than one active agent the device may contact each agent separately (in any order), the agents simultaneously or one or more agent at a time.

The invention also relates to contact lens care solutions containing one or more $C_8$ to $C_{16}$ fatty acids and/or fatty acid esters and preferably an androgen or androgen analogue and/or an anti-inflammatory agent in which the contact lens is soaked prior to being fitted to the eye of the subject to treat, prevent or reduce the occurrence of an eye disorder or its symptoms. Preferably the eye disorder is dry eye. The contact lens may be soaked in one or more solutions each containing one or more of the active agents. Exemplary fatty acids and/or fatty acid esters, androgens, androgen analogues and/or anti-inflammatory agents are disclosed herein. The contact lens care solution may treat or prevent one or more forms of dry eye discussed herein.

The present invention also relates to the use of a therapeutically effective amount of one or more $C_8$ to $C_{16}$ fatty acids and/or fatty acid esters and preferably androgen or an analogue thereof for the manufacture of a medicament for the prevention and/or treatment of dry eye disorders including one or more of the following: aqueous-deficient dry eye; evaporative dry eye and dry eye disorders caused by the wearing of an ophthalmic device such as a contact lens Sjögren's syndrome; an autoimmune disorder; non-Sjögren aqueous-deficient DED resulting from lacrimal gland insufficiency; lacrimal duct obstruction; meibomian gland disease; blepharitis; eyelid aperture disorders; conjunctival disorders and blink disorders. Typically, the subject is first assessed as needing treatment for dry eye disorder, likely to need treatment for dry eye, being at risk of developing dry eye, or being at particular risk (e.g. from complications or consequence of developing the condition) if dry eye is developed, such that preventing or inhibiting the development of dry eye or treating the dry eye disorder was considered necessary.

The present invention also relates to a method of making an ophthalmic device for the prevention and/or treatment of dry eye, by a therapeutically effective amount of one or more $C_8$ to $C_{16}$ fatty acids and/or fatty acid esters and preferably androgen or an analogue thereof, comprising the step of contacting an ophthalmic device with a solution comprising one or more. $C_8$ to $C_{16}$ fatty acids and/or fatty acid esters and preferably androgen or an analogue thereof and then applying the device to the eye. In certain embodiments, the ophthalmic device is a contact lens. In certain embodiments, the contact lens is a soft contact lens. The lens may be prepared by soaking the lens in a care solution comprising: $C_8$ to $C_{16}$ fatty acids and/or fatty acid esters and preferably an androgen or androgen analogue. The lens may be soaked in the solution for 15 mins to 3 hours. In certain applications the lens may be soaked for 10 mins to 15 mins, 15 mins to 30 mins, 20 mins to 1 hour, 30 mins to 1 hour 45 mins to 1.5 hours, 45 mins to 1.25 hours 45 mins to 2 hours or other acceptable time periods. In some instances, the contact lens may be stored in the contact lens care solution overnight. The lens may also be prepared by a) $C_8$ to $C_{16}$ fatty acids or fatty acid esters and preferably androgen or an analogue thereof incorporated liposomes that are attached to the lens surface and/or b) a care solution formulation of $C_8$ to $C_{16}$ fatty acids or fatty acid esters and preferably androgen or an analogue thereof being incorporated into the packaging solution in the case of disposable lenses (e.g. daily lenses). The $C_8$ to $C_{16}$ fatty acids or fatty acid esters and preferably androgen or an analogue thereof is desirably present in the solution in an amount ranging from 6 to 25 µg/ml. Other concentrations disclosed herein may also be used. Preferably, there is an amount of fatty acid and/or fatty acid ester that is associated with the contact lens sufficient to achieve a tear film concentration of about 5 to 50 µg/ml, preferably 10 µg/ml, in use.

Embodiments of the invention in which the $C_8$ to $C_{16}$ fatty acids and/or fatty acid esters are released from an ophthalmic device are advantageous in that the device (such as a contact lens) maintains the solution in contact with the eye-lid when the wearer blinks, as opposed to eye drops or a spray which may be relatively quickly drained off the eye by the normal tear flush. Without being bound by any theory or particular mode of action it is believed that fatty acids and/or fatty acid esters are absorbed into the matrix of the device or coated onto the surface of the device when soaked in the care solution. The fatty acids and/or fatty acid esters may then be released from the contact lens into the treatment area (for example, upper tarsal conjunctiva of the upper eyelid or the lid margin).

The present invention also relates to use of an amount of one or more $C_8$ to $C_{16}$ fatty acids or fatty acid esters therapeutically effective to inhibit lipase activity while permitting bacterial growth (ie without having antibacterial activity) in the preparation of a medicament for the prevention or treatment of an eye disorder in a subject. The eye disorder is preferably dry eye.

The present invention also relates to a composition for the prevention and/or treatment of an eye disorder in a subject wherein the active is one or more $C_8$ to $C_{16}$ fatty acids or fatty acid esters in an amount therapeutically effective to inhibit lipase activity while permitting bacterial growth (ie without having antibacterial activity).

The present invention also relates to use of an amount of one or more $C_8$ to $C_{16}$ fatty acids and/or fatty acid esters therapeutically effective to inhibit lipase activity without substantially altering the dynamic microbial community of the eye with minimal or insubstantial antibacterial activity in the preparation of a medicament for the prevention or treatment of an dry eye disorder in a subject. The invention also relate to use of an amount of one or more $C_8$ to $C_{16}$ fatty acids and/or fatty acid esters therapeutically effective to inhibit lipase activity without substantially altering the dynamic microbial community of the eye with no antibacterial activity in the preparation of a medicament for the prevention or treatment of an dry eye disorder in a subject.

The present invention relates to compositions for the prevention and/or treatment of a dry eye disorder in a subject, wherein the active is one or more $C_8$ to $C_{16}$ fatty acids and/or fatty acid esters in an amount therapeutically effective to inhibit lipase activity without substantially altering the dynamic microbial community of the eye. Typically, the composition has minimal or insubstantial antibacterial activity. Certain embodiments relate to compositions for the prevention and/or treatment of a dry eye disorder in a subject wherein the active is one or more $C_8$ to $C_{16}$ fatty acids and/or fatty acid esters in an amount therapeutically effective to inhibit lipase activity without substantially altering the dynamic microbial community of the eye with no antibacterial activity. Certain embodiments also relate to compositions for the prevention and/or treatment of a dry eye disorder in a subject, wherein the active is one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase activity without substantially altering the dynamic microbial community of the eye with minimal or insubstantial antibacterial activity. Certain embodiments also relate to compositions for the prevention and/or treatment of a dry eye disorder in a subject, wherein the active is one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or a combination thereof in an amount therapeutically effective to inhibit lipase activity without substantially altering the dynamic microbial community of the eye with no antibacterial activity.

Certain embodiments are directed to one or more $C_8$ to $C_{16}$ fatty acids and/or fatty acid esters for use in preventing or treating an eye disorder in a subject, wherein the $C_8$ to $C_{16}$ fatty acids and/or fatty acid esters are therapeutically effective to inhibit lipase activity without substantially altering the dynamic microbial community of the eye with minimal or insubstantial antibacterial activity. In another embodiment, one or more $C_8$ to $C_{16}$ fatty acids and/or fatty acid esters may be used for preventing or treating an eye disorder in a subject, wherein the $C_8$ to $C_{16}$ fatty acids and/or fatty acid esters are therapeutically effective to inhibit lipase activity without substantially altering the dynamic microbial community of the eye with no antibacterial activity.

The present invention also provides glycerol monolaurate and/or lauric acid for use in preventing or treating an eye disorder in a subject, wherein the glycerol monolaurate and/or lauric acid is therapeutically effective to inhibit lipase activity while permitting commensal bacterial growth of the eye. Preferably, the disorder is a dry eye disorder.

In another embodiment there is provided a kit for use in a method of the invention mentioned above, the kit including a container holding one or more $C_8$ to $C_{16}$ fatty acids or fatty acid esters or pharmaceutical composition or contact lens care solution of the invention and a label or package insert with instructions for use. Optionally, the kit includes a vessel for containing a contact lens soaking in the composition or contact lens care solution and/or a device for dispensing eye-drops. In certain embodiments, the kit may contain one or more further ingredients for the prevention and/or treatment of dry eye disorders.

BRIEF DESCRIPTION OF THE DRAWINGS

Features, aspects, and advantages of the present disclosure will become better understood with regard to the following description, appended claims, and accompanying figures.

FIGS. 5A and 5B shows percentage reduction of lipase in strains cultured with various µg/ml concentrations of glycerol monolaurate or lauric acid for 24 hours.

DETAILED DESCRIPTION OF THE INVENTION

Figure 1A:
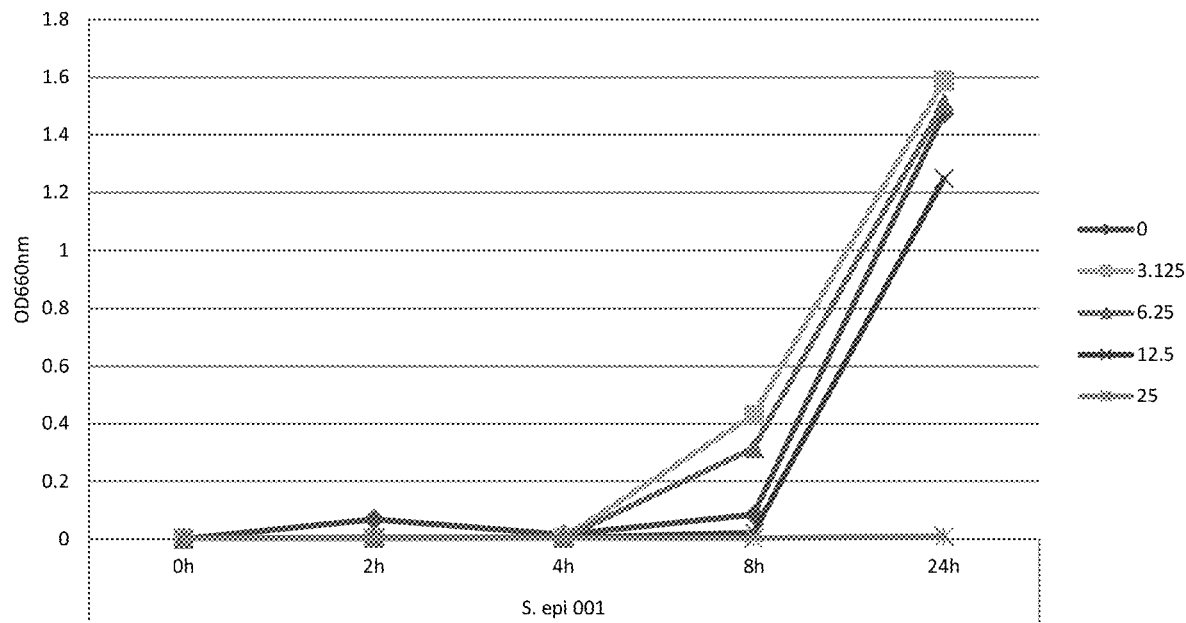
FIGS. 1A, 1B, 1C, 1D, and 1E shows the effect of various µg/ml concentrations of glycerol monolaurate on growth of several strains of bacteria.

The present disclosure is described in further detail with reference to one or more embodiments, some examples of which are illustrated in the accompanying drawings. The examples and embodiments are provided by way of explanation and are not to be taken as limiting to the scope of the disclosure. Furthermore, features illustrated or described as part of one embodiment may be used by themselves to provide other embodiments and features illustrated or described as part of one embodiment may be used with one or more other embodiments to provide further embodiments. The present disclosure covers these variations and embodiments as well as other variations and/or modifications.

The term "comprise" and its derivatives (e.g., comprises, comprising) as used in this specification is to be taken to be inclusive of features to which it refers, and is not meant to exclude the presence of additional features unless otherwise stated or implied.

The features disclosed in this specification (including accompanying claims, abstract, and drawings) may be replaced by alternative features serving the same equivalent or similar purpose, unless expressly stated otherwise.

It will be understood that the invention disclosed and defined in this specification extends to all alternative combinations, of two or more of the individual features mentioned or evident from the text or drawings. All of these different combinations constitute various alternative aspects of the invention.

The subject headings used in the detailed description are included for the ease of reference of the reader and should not be used to limit the subject matter found throughout the disclosure or the claims. The subject headings should not be used in construing the scope of the claims or the claim limitations.

As discussed herein, it has been found that a $C_8$ to $C_{16}$ fatty acids and/or fatty acid ester, for example, glycerol monolaurate and/or lauric acid, are effective to inhibit lipase activity and thus, useful to treat, reduce and/or prevent dry eye. The invention disclosed herein has been found useful for alleviating symptoms associated with dry eye disorders. The invention disclosed herein has also been found useful for preventing or reducing dry eye, including when associated with contact lens wear. The present disclosure is also directed to methods of for treating, reducing or preventing such diseases or conditions.

Dry eye is a disorder of the eye due to tear deficiency or excessive evaporation, which causes damage to the ocular surface and is associated with symptoms of ocular discomfort, such as itchiness, irritation foreign body sensation, redness, photophobia, pain and paradoxical tearing from corneal irritation. Dry eye disorders have been attributed to either decreased tear production (aqueous-deficient dry eye) and/or excessive tear evaporation (evaporative dry eye). Dry eye disorders may be caused by one or more of the following: the wearing of the ophthalmic device such as a contact lens, Sjögren's syndrome, an autoimmune disorder, non-Sjögren aqueous-deficient Dry eye disorder resulting from lacrimal gland insufficiency, lacrimal duct obstruction, meibomian gland disease, blepharitis, eyelid aperture disorders, conjunctival disorders and/blink disorders Glycerol monolaurate (also referred to as GML) is the fatty acid ester of lauric acid and glycerol. It is commonly used as a surfactant, emulsifier and preservative. It is used as a food additive (for example in ice-cream) or used in cosmetics and soaps. The structure of glycerol monolaurate is shown below:

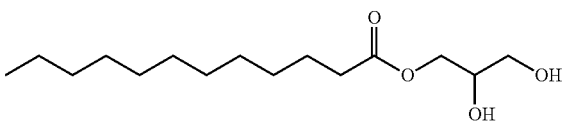 [SMILES: CCCCCCCCCCCC(=O)OCC(O)CO]

Lauric acid is a fatty acid commonly used in the production of cosmetics and soaps. The structure of lauric acid is shown below:

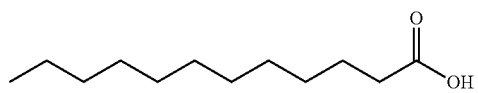

As used herein reference to a fatty acid or fatty acid ester by the nomenclature $C_x$ is reference to a fatty acid or fatty acid ester with x carbon atoms in a main chain or backbone. For example, $C_8$ to $C_{16}$ fatty acids and/or fatty acid esters have a main chain of 8 to 16 carbon atoms. The fatty acids or fatty acid esters may be saturated or unsaturated. Saturated fatty acid or fatty acid esters are preferred.

The term "androgen" refers to a class of compounds that bind to androgen receptors. Androgens are typically steroid hormones and include, for example, testosterone, dihydrotestosterone and androstenedione.

The terms "treating" or "treatment" refer to administering to a subject a therapeutically effective amount of an active such that the subject has an improvement in the condition to be treated (e.g. dry eye). Treatment may prevent worsening of the condition, improve the condition, but may not provide a complete cure for the condition. Efficacy of treatment may be determined by clinical assessment including the Schirmer test without anaesthesia, tear breakup time (TBUT), phenol thread test, corneal staining or tear film triglyceride levels.

The terms "preventing" or "prevention" refer to administering to a subject a therapeutically effective amount of an active, such that the signs and/or symptoms of a condition (e.g. dry eye) are averted, delayed or significantly reduced in frequency in the subject, relative to a subject who does not receive the composition. Prevention does not require that the condition or symptoms are permanently avoided. In addition, the term "prevention" is used in its clinical sense to mean inhibit a disease, condition or disorder from occurring, rather than in an absolute sense of making it impossible for the disease, condition or disorder to ever occur in a given subject. Hence, inhibition of progression to disease, disorder or reduced new disease or disorder amounts to "prevention" within the meaning of this specification, even if there is pre-existing disease or disorder.

The terms "therapeutically effective amount" or "effective amount" refer to an amount of an active that results in an improvement or remediation of the symptoms of a disease or condition.

The term "ophthalmic device" refers to an object that resides in or on the eye. The device may provide optical correction or may be cosmetic. Ophthalmic devices include but are not limited to contact lenses (including soft contact lenses), intraocular lenses, onlay lenses, ocular inserts, punctal plugs, and optical inserts. The ophthalmic devices include contact lenses, such as soft contact lenses, made from silicone elastomers or hydrogels, which include, but are not limited, to silicone hydrogels and fluorohydrogels. The ophthalmic devices may be "single-use" devices e.g. single-use or daily contact lenses.

The term "administering" or "administration" means placing the active, composition or ophthalmic device onto the surface of the eye, or in the eye and/or ocular adnexa for example, lid margins, puncta, skin around the eye lids of a subject or administering it orally. Typically such a device (for example, a soft contact lens) is in contact with the anterior surface of the subject's eye for a length of time such as 8 to 16 hours daily. Alternatively, the active or composition may be placed into or onto an ocular insert as a method of drug delivery. Typically such an ocular insert is inserted into the space between the lids and the sclera (fornix) and gradually releases the drug. Alternatively, a biodegradable collagen lens soaked in the active or composition may be placed onto the surface of the eye, or inserted into the eye, of a subject. Typically the collagen lens slowly dissolves and improves patient symptoms. Alternatively, the active or composition may be incorporated into an ointment as a method of drug delivery. Typically, the ointment may be applied into the space between the lids and the sclera of the eye or applied onto the lid margins.

As used herein "without substantially altering the dynamic commensal microbial community of the eye" means without substantially altering the growth, viability, numbers, relative amounts and/or types of commensal bacteria, fungi or viruses commonly found or pre-existing in the eye. Typically, the commensal bacteria referred to are those bacterial types at levels commonly found in a healthy eye. Determining the bacterial component of the dynamic commensal microbial community associated with the eye to assess if it is substantially altered, may be by any suitable method including by taking an ocular swab of a subject and then (a) plating the bacteria from the swab onto agar plates to determine number of colonies, or (b) sequencing 16s ribosomal DNA or RNA. 16S rRNA gene sequences contain hypervariable regions that can provide species-specific signature sequences useful for bacterial identification.

In some embodiments, the minimal antibacterial activity is a 10% or 5% reduction numbers of total bacteria, or of a specific type of commensal bacteria, as measured by any suitable method including those described herein.

As used herein "while permitting bacterial growth" means that there is sufficiently low bactericidal or bacteriostatic activity so that bacteria, particularly commensal bacteria of the eye, are capable of growth. Determining bacterial growth can be by any suitable method including those described herein, including as per Example 1.

The subject is a subject that that has one or more of the following: suffers from dry eye disorder, is at risk of suffering from dry eye disorder, is at particular risk if dry eye disorder is developed, is a contact lens wearer and a suitable candidate for wearing contact lenses. The subject may suffer from or be at risk of suffering from other disease states disclosed herein. The subject may be a human or an animal subject. The subject is preferably human. A subject may be identified as suffering from or at risk of developing a dry eye disorder using any one of the following assessment methods: Schrimer test without anaesthesia, tear break-up time (TBUT), lipid layer appearance, phenol thread test, corneal staining, telanglectasia, lip wiper epithellopathy, gland expressibility, meibography, intraocular pressure and Ocular Surface Disease Index (OSDI) questionnaire to assess the subject's perception of dry eye severity.

Certain compositions of the present invention may be ophthalmic compositions, which are compositions suitable for administration to the eye. Examples of ophthalmic compositions are suspensions, ointments, gels, sprays, creams, sustained release formulations and/or solutions suitable for application as an eye drop. In certain embodiments, the composition may be applied directly to a contact lens and/or otherwise be a contact lens care solution in which the contact lens is soaked, prior to being fitted to the subject's eye. Without being bound by any theory or particular mode of action, it is believed that that this would allow for the active to be absorbed into the matrix of the contact lens or coated onto or into the surface of the contact lens, then slowly released into or onto the treatment area, particularly the eyelid and/or upper tarsal conjunctiva, once fitted to the eye.

Aqueous solutions (including those released from soft contact lenses) are typically useful, based on ease of formulation, as well as a subject's ability to easily administer such compositions by means of instilling one to two drops of the solution in the affected eyes. In the case of contact lenses, the administration of the solution is simplified in that the contact lens and the solution are applied in the one step. However, the compositions may also be suspensions, viscous or semi-viscous gels, or other types of solid or semi-solid compositions such as ointments and creams. The ointments have the advantage that they are slowly absorbed and thus provide for sustained release.

In the case of a spray, the composition may be applied to the inside of the eyelid. The composition disclosed herein may also be applied as a solution whereby soft contact lenses, including silicone hydrogel lenses, may absorb the solution or coat the surface and then release it when fitted on the eye. The contact lens maintains the solution in contact with the eye-lid when the wearer blinks, as opposed to eye drops or a spray which may be relatively quickly drained off the eye by the normal tear action.

A variety of carriers may be used in the compositions disclosed herein including one or more of the following: water, mixtures of water and water-miscible solvents, such as $C_1$- to $C_7$-alkanols; vegetable oils or mineral oils comprising from 0.5 to 5% non-toxic water-soluble polymers; gelling products, such as gelatin, alginates, pectins, tragacanth, karaya gum, xanthan gum, carrageenan, agar and acacia, and their derivatives; starch derivatives, such as starch acetate and hydroxypropyl starch; cellulose and its derivatives and also other synthetic products, such as polyvinyl alcohol, polyvinylpyrrolidone, polyvinyl methyl ether, polyethylene oxide, cross-linked polyacrylic acid, such as neutral Carbopol, or, mixtures of those polymers; naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan mono-oleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those mentioned herein.

The composition according to the present invention may comprise at least one gelling agent. Gelling agents suitable for use in pharmaceutical compositions are known to those of ordinary skill in the art and include, for example one or more of the following: xanthan gum and its derivatives; carbomer and its derivatives; acrylate based copolymers and cross polymers; sodium polyacrylate and its derivatives; cellulose and its derivatives; and starch and agar and their derivatives.

In certain embodiments, the selection of the gelling agent may involve selecting a gelling agent that provides a clear gel, a substantially clear gel, or an acceptably clear gel. The amount of gelling agent added to the composition may be readily determined by one of ordinary skill in the art with a minimum of experimentation, and will depend upon factors known to those skilled in the art, such as the properties of the gelling agent and the desired properties of the composition.

Additional ingredients that may be included in the compositions of the invention include surfactant, anti-oxidants, tonicity enhancers, preservatives, stabilizers, non-toxic excipients, demulcents, sequestering agents, pH adjusting agents, co-solvents, viscosity building agents or combinations thereof.

For the adjustment of the pH, for example, to a physiological pH, buffers may be useful. The pH of the present solutions typically may be maintained within the range of between 6.5 to 8.0. Other ranges may also be used, for example, between 7.2 to 7.5, between 6.8 to 7.2 or between 7.3 to 7.5. Selecting a pH or pH range that is compatible, or substantially compatible, with the ocular surface is typically desired. Suitable buffers may be added, such as one or more of the following: boric acid; sodium borate; potassium citrate; citric acid; sodium bicarbonate; and TRIS, disodium edetate (EDTA) and various phosphate buffers (including combinations of NaCl, KCl, $Na_2HPO_4$, $NaH_2PO_4$ and $KH_2PO_4$) and mixtures thereof. In certain embodiments, the buffer used contains concentrations of about NaCl 8 g/L, KCl 0.2 g/L, $Na_2HPO_4$ 1.15 g/L and $KH_2PO_4$ 0.2 g/L.

Tonicity is adjusted if needed typically by tonicity enhancing agents. Such agents may, for example, be of ionic and/or non-ionic type. Examples of ionic tonicity enhancers are alkali metal or earth metal halides, such as, for example one or more of the following: $CaCl_2$, KBr, KCl, LiCl, NaI, NaBr or NaCl, $Na_2SO_4$ and boric acid. Non-ionic tonicity enhancing agents are, for example, urea, glycerol, sorbitol, mannitol, propylene glycol, dextrose or combinations thereof. In certain embodiments, the aqueous solutions may be adjusted with tonicity agents to approximate the osmotic pressure of normal lachrymal fluids.

In certain embodiments, the compositions of the invention additionally comprise a preservative. A preservative may typically be selected from a quaternary ammonium compound such as benzalkonium chloride (N-benzyl-N—($C_8$-$C_{18}$-alkyl)-N,N-trimethylammonium chloride), benzoxonium chloride or the like. Examples of preservatives different from quaternary ammonium salts are alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, sodium benzoate, salicylic acid, alcohols, such as, for example, chlorobutanol, benzyl alcohol or phenyl ethanol, guanidine derivatives, such as, for example, chlorohexidine or polyhexamethylene biguanide, sodium perborate, Germal® π or sorbic acid. In certain embodiments, preservatives such quaternary ammonium compounds, in particular benzalkonium chloride or its derivative such as Polyquad, alkyl-mercury salts and parabens may be used. Other suitable preservatives include polymyxin B sulphate and Purite®. Where appropriate, a sufficient amount of preservative is added to the ophthalmic composition to ensure protection against secondary contamination during use caused by bacteria and fungi. In certain embodiments, the compositions of this invention do not include a preservative, is are preservative free. Such formulations would be useful for subjects who wear contact lenses.

In certain embodiments, the compositions additionally may comprise a surfactant. A surfactant may typically be selected from but not limited to Sodium Lauryl Sulphate BP, Sorbitan esters: Spans, Sorbitan monooleate, Polyoxyethylene glycol sorbitan alkyl esters: Polysorbate Block copolymers of polyethylene glycol and polypropylene glycol: Poloxamers and the quaternary ammonium and pyridinium cationic surfactants.

In other embodiments, the compositions additionally may comprise an anti-oxidants. An anti-oxidant may typically be selected from but not limited to: glutathione, vitamin C, vitamin A, and vitamin E, ascorbic acid and tocopherols, gallates, Glucam E-20 Butylated hydroxyanisole (BHA) and butylated hydroxytoluene (BHT).

The compositions disclosed herein may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements.

Other compounds may also be added to the compositions of the present invention to increase the viscosity of the carrier. Examples of viscosity enhancing agents include, but are not limited to: polysaccharides, chondroitin sulfate and its salts, dextrans, various polymers of the cellulose family; vinyl polymers; acrylic acid polymers and/combinations thereof.

In certain embodiments, the composition may be administered in ways that are deemed suitable by a person of ordinary skill in the art. The composition may be administered topically or orally. The composition of the invention may be administered in single or multiple doses and for various length of times until the disease or condition is either completely treated or until the desired level of treatment has been achieved. The person of ordinary skill in the art will recognise that the dosage amount, dosage regimen and length of treatment may depend on factors such as, for example, the disease type, the location, the severity of the disease or disorder, need to alleviate symptoms and the health of the subject. In the case of a contact lens care solution, the composition may be administered once a day (when the contact lens is applied). Alternatively, the contact lens may be stored in the care solution (e.g. overnight) whilst not being worn by the subject. In the case of eye drops, the composition may be administered every two to four hours or more frequently for example every half hourly when subject has severe symptoms. In the case of ointment or cream, the composition may be administered every two to four hours. When administered orally, the composition may for example, be taken one to two times a day.

In certain embodiments, the ophthalmic device containing the $C_8$ to $C_{16}$ fatty acids and/or related fatty acid esters, for example, glycerol monolaurate and/or lauric acid, may be prepared by contacting the ophthalmic device with a solution containing the $C_8$ to $C_{16}$ fatty acids and/or related fatty acid esters. Where there is a combination of more than one fatty acid and/or fatty acid ester the ophthalmic device may be contacted with either one solution or a series of solutions containing one or more of the fatty acids or fatty acid esters. Similarly if the ophthalmic device additionally contains androgen or androgen analogue and/or an anti-inflammatory agent, the ophthalmic device may be contacted with a single solution containing or a series of solutions containing one or more of the fatty acids and/or fatty acid ester and androgen, androgen analogue and/or anti-inflammatory agent. The above actives may be contacted with the ophthalmic device prior to selling or delivering the ophthalmic device to a subject (e.g. adding the active(s) to one or more solutions prior to sealing the package, and subsequently sterilizing the package) or during the preparation of the ophthalmic device. Where one or more active ingredient is contacted to the ophthalmic device prior to selling or delivering the ophthalmic device, the other actives may be contacted to the ophthalmic device during preparation of the ophthalmic device. As discussed herein, in certain embodiments, one or more of the actives are incorporated into liposomes which are attached to the device (such as a lens) and which then permit the actives to be released during wearing of the device.

Sterilization can take place at different temperatures and periods of time. In certain embodiments, sterilization is carried out using filter sterilization.

The solutions that are used in one or more of the disclosed methods may be water-based (i.e. aqueous) solutions. Typical solutions include saline solutions, other buffered solutions, deionized water or combinations thereof. For example, an aqueous solution is deionized water or saline solution containing salts including sodium chloride, sodium borate, sodium phosphate, sodium hydrogen phosphate, sodium dihydrogenphosphate, the corresponding potassium salts of the same or combinations thereof. These ingredients are generally combined to form buffered solutions that include an acid and its conjugate base, so that addition of acids and bases cause a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol,n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. For example, the solution is a borate buffered or phosphate buffered saline solution or deionized water. For example, the solution contains about NaCl 8 g/L, KCl 0.2 g/L, $Na_2HPO_4$ 1.15 g/L and $KH_2PO_4$ 0.2 g/L buffer.

The kit or article of manufacture may comprise a container and a label or package insert on or associated with the container. Suitable containers include, for example, bottles, vials, syringes, blister pack, tubes etc. The containers may be formed from a variety of materials such as metal, glass or plastic. The container holds the composition which is effective for treating the condition and may have a sterile access port (for example the container may be an intravenous solution bag or a vial having a stopper piercable by a hypodermic injection needle). The label or package insert indicates that the composition is used for treating the condition of choice. In certain embodiments, the label or package insert includes instructions for use and indicates that the therapeutic composition may be used to prevent, reduce and/or treat dry eye. Where the composition comprises $C_8$ to $C_{12}$ fatty acid and/or fatty acid ester, an additional container may comprise androgen or androgen analogue and/or an anti-inflammatory agent. Alternatively, the anti-inflammatory agent may be contained in a separate container.

The kit may comprise (a) a $C_8$ to $C_{16}$ fatty acid or fatty acid ester, a composition or contact lens care solution as described above; and (b) a second container comprising a solution that is suitable for application to the eye, carriers, excipients, and the like. The kit in this embodiment of the invention may further comprise one or more package inserts. The inserts, for example, indicate how the $C_8$ to $C_{16}$ fatty acid and/or fatty acid ester composition and the excipient may be used to prevent, reduce and/or treat dry eye, and provide instructions for use of the kit.

The second container may comprise a solution that is suitable for application to the eye (e.g. an aqueous solution) and/or pharmaceutically-acceptable buffers, such as bacteriostatic water for injection (BWFI), phosphate-buffered saline, Ringer's solution and dextrose solution. It may further include other materials desirable from a commercial and user standpoint, including other buffers, diluents, filters, needles, and syringes. It will be understood that the invention disclosed and defined in this specification extends to all alternative combinations of two or more of the individual features mentioned or evident from the text or drawings. All of these different combinations constitute various alternative aspects of the invention.

EXAMPLES

The present invention will now be more fully described with reference to the accompanying examples and drawings. It should be understood, however, that the description following is illustrative only and should not be taken in any way as a restriction on the generality of the invention described above.

Example 1

One aspect of this invention is inhibition of lipase activity without substantial antibacterial activity. This example illustrates one readily available assay for lipase activity and bacterial growth in certain conditions; especially concentration of active, time and bacterial species. In the following example, lipase activity and bacterial growth has been assayed in four different strains of bacteria following treatment with various concentrations of glycerol monolaurate or lauric acid.

The bacterial strains *S. aureus* 020 & 134, and *S. epidermidis* 024 & 025 were grown at 37° C. in TSB treated with 0, 6.25 or 12.5 μg/ml of glycerol monolaurate or lauric acid as well as in TSB extraction of glycerol monolaurate ointment prior to assay of bacterial growth and lipase activity. After incubation for 24 h, bacterial growth was determined by measuring the optical density of cultures using a spectrophotometer at a wavelength of 660 nm. Lipase activity by test bacterial strains under various treatments were assessed by examining the lipase activity in bacterial culture supernatants with a QuantiChrom™ Lipase Assay Kit. The results of the experiment are presented in Tables 1-4 below. The data show that glycerol monolaurate inhibits lipase activity by approximately 16-88% (Table 1), lauric acid inhibits lipase activity by approximately 46-72% (Table 2), and extractions of glycerol monolaurate ointment of composition 14 (contents outlined below) inhibit lipase activity by approximately 51-77% (Tables 3 and 4), when used at concentrations that do not substantially inhibit growth of the bacterial strains.

TABLE 1

| Strain | Glycerol monolaurate (µg/ml) | Inhibition of Growth | Inhibition of Lipase activity |
|---|---|---|---|
| S. aureus 020 | 5 | 1% | 16% |
|  | 7.5 | 0 | 29% |
|  | 10 | 4% | 50% |
|  | 12.5 | 4% | 63% |
|  | 15 | 2% | 73% |
|  | 17.5 | 0 | 88% |
| S. aureus 134 | 10 | 0 | 25% |
|  | 12.5 | 0 | 38% |
|  | 15 | 1% | 49% |
|  | 17.5 | 0 | 63% |
| S. epidermidis 024 | 6.25 | 0 | 46% |
|  | 12.5 | 0 | 70% |
| S. epidermidis 025 | 6.25 | 0 | 48% |
|  | 12.5 | 0 | 72% |

TABLE 2

| Strain | Lauric acid (µg/ml) | Inhibition of Growth | Inhibition of Lipase activity |
|---|---|---|---|
| S. epidermidis 024 | 6.25 | 0 | 46% |
|  | 12.5 | 0 | 70% |
| S. epidermidis 025 | 6.25 | 0 | 48% |
|  | 12.5 | 0 | 72% |

TABLE 3

| Strain | Ointment extraction in TSB | Inhibition of Growth | Inhibition of Lipase production |
|---|---|---|---|
| S. aureus 020 | GML0.01% + TT0.02% | 0 | 71% |
|  | GML0.025% + TT0.02% | 0 | 77% |

* TT—testosterone, GML—Glycerol monolaurate, TSB—Tryptone Soy Broth

TABLE 4

| Strain | Ointment extraction in TSB | Inhibition of Growth | Inhibition of Lipase activity |
|---|---|---|---|
| S. aureus 020 | GML0.025% | 4% | 51% |
|  | GML0.05% | 2% | 59% |

* GML—Glycerol monolaurate, TSB—Tryptone Soy Broth

Example 2

Figure 1B:
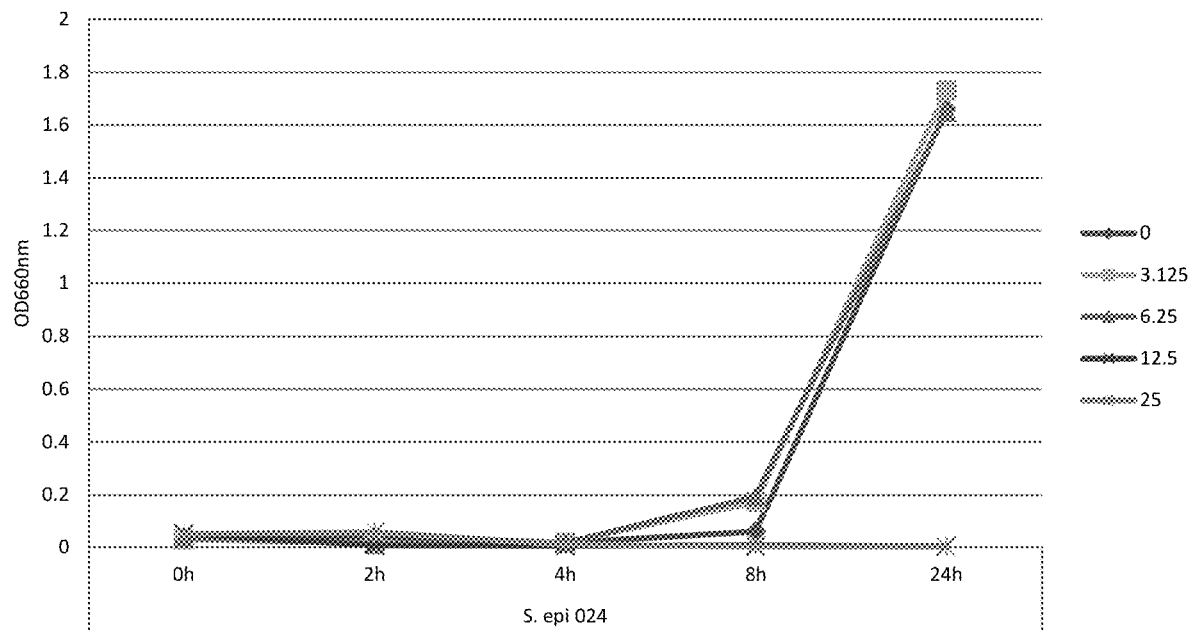
Figure 1C:
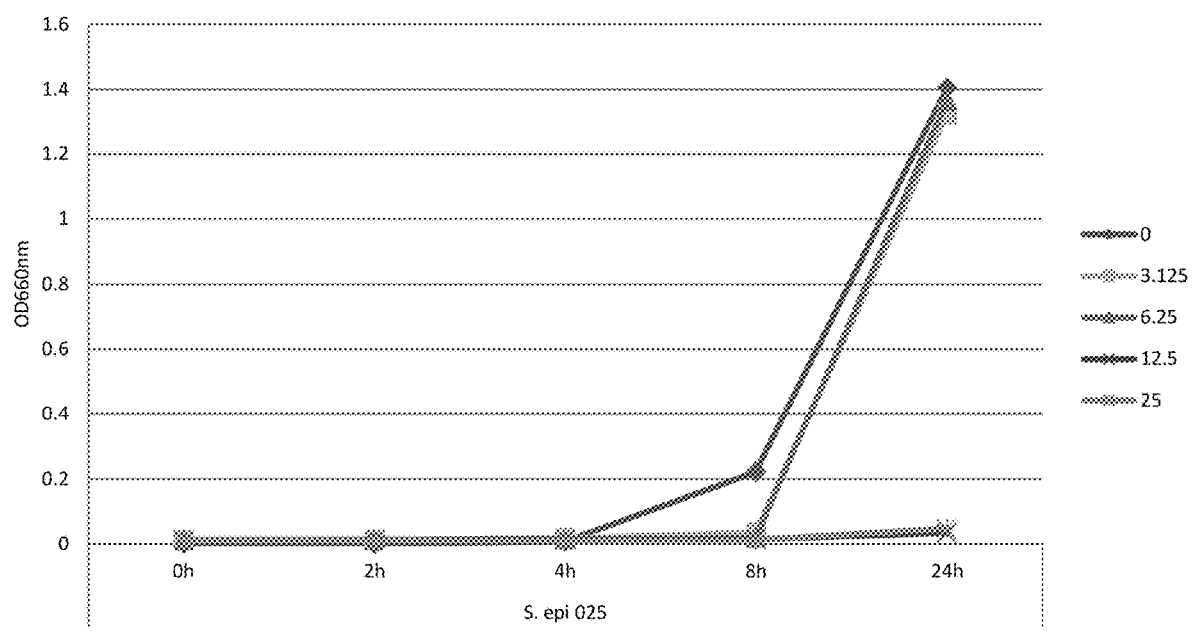
Figure 1D:
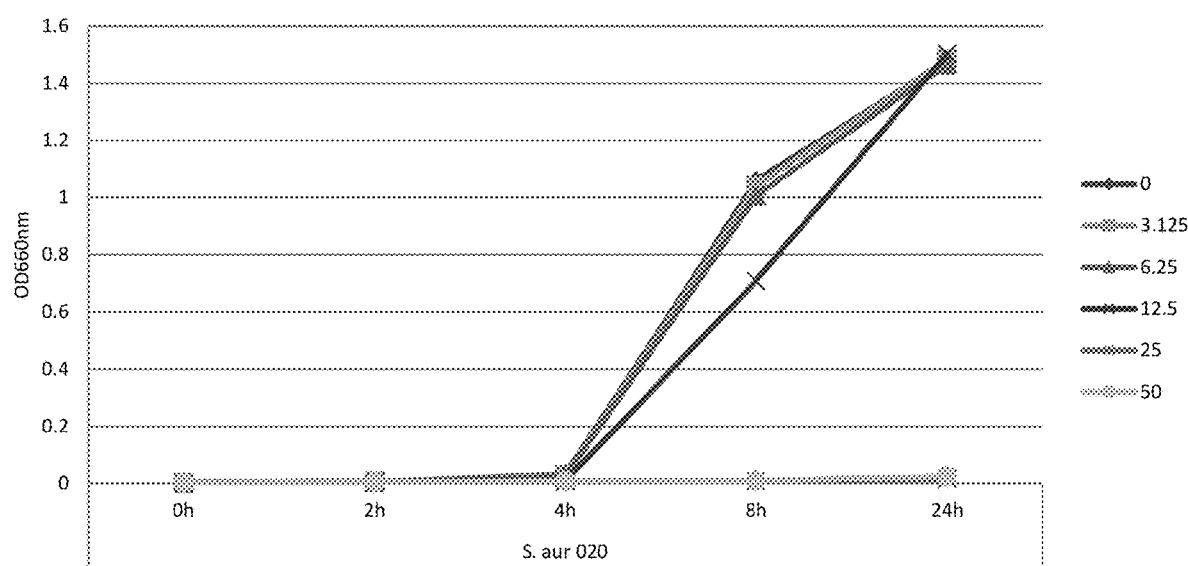
Figure 1E:
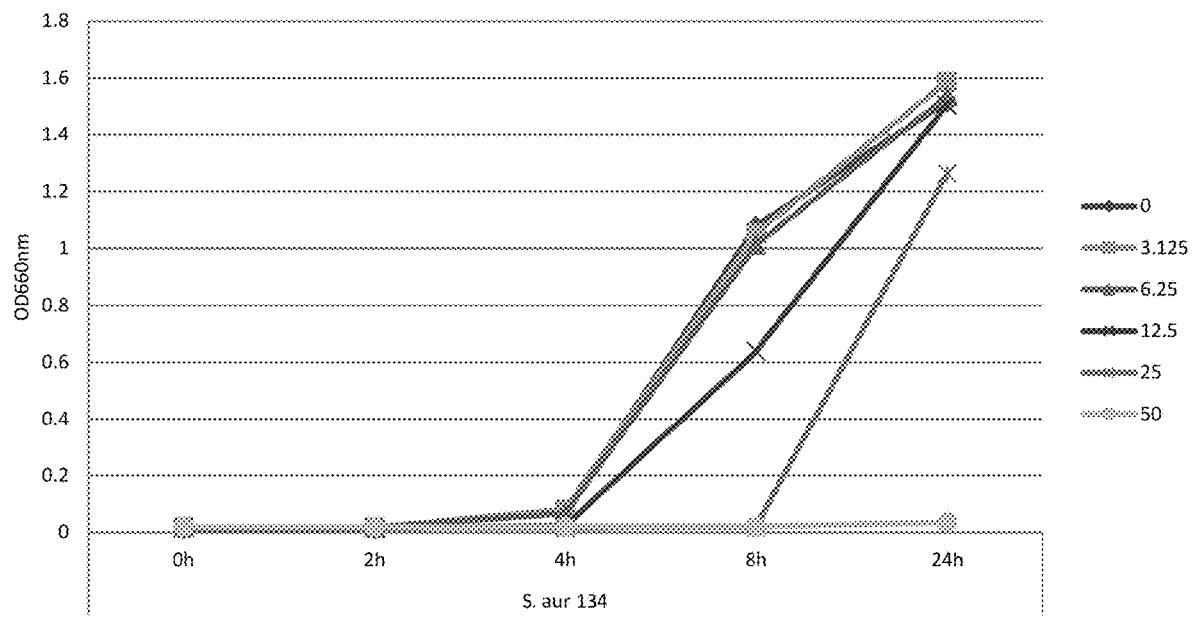
Figure 2A:
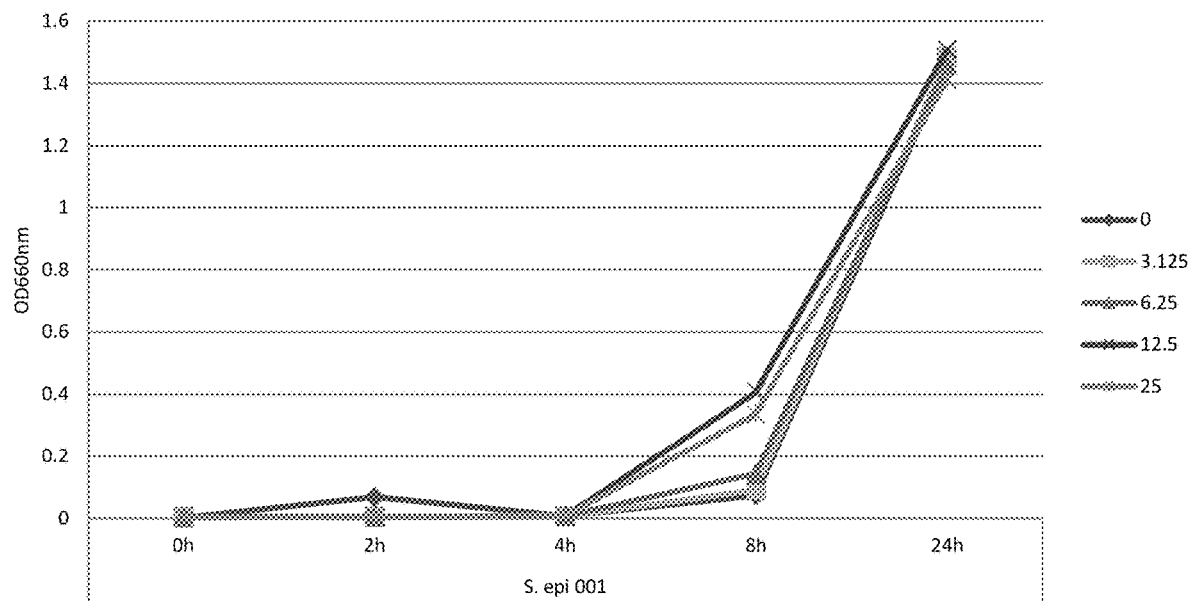
FIGS. 2A, 2B, 2C, 2D, and 2E shows the effect of various µg/ml concentrations of lauric acid on growth of several strains of bacteria.
Figure 2B:
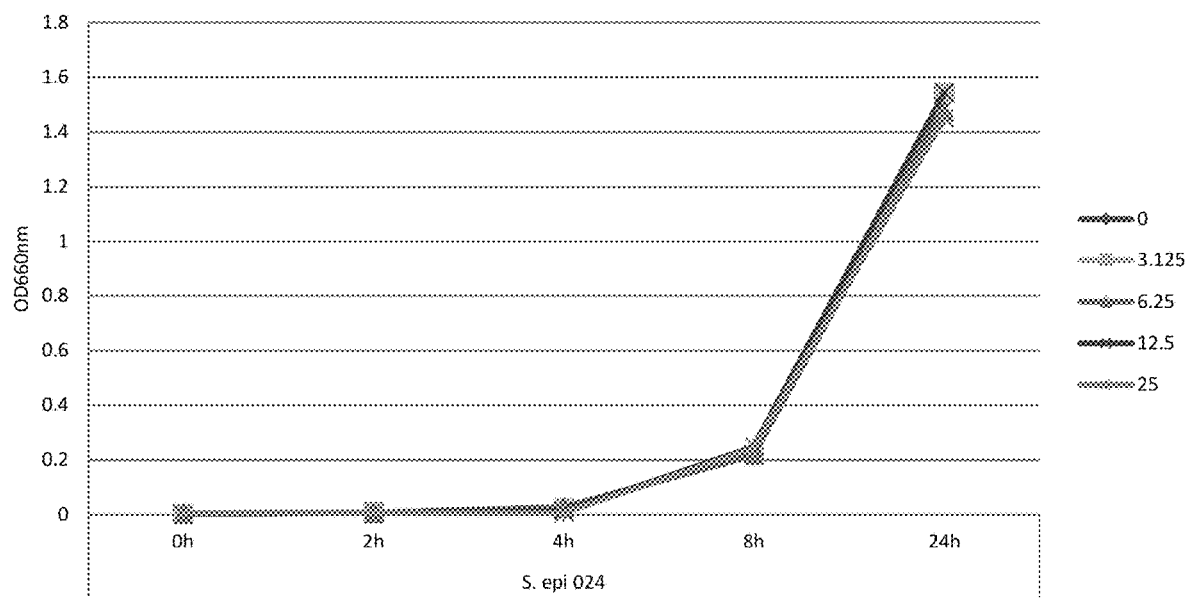
Figure 2C:
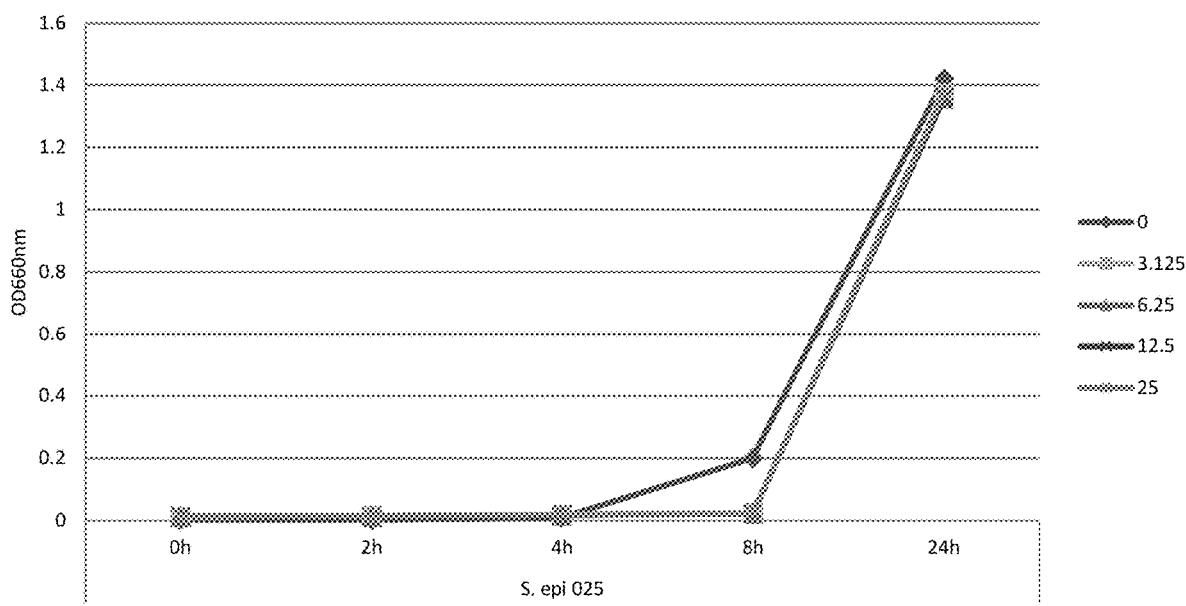
Figure 2D:
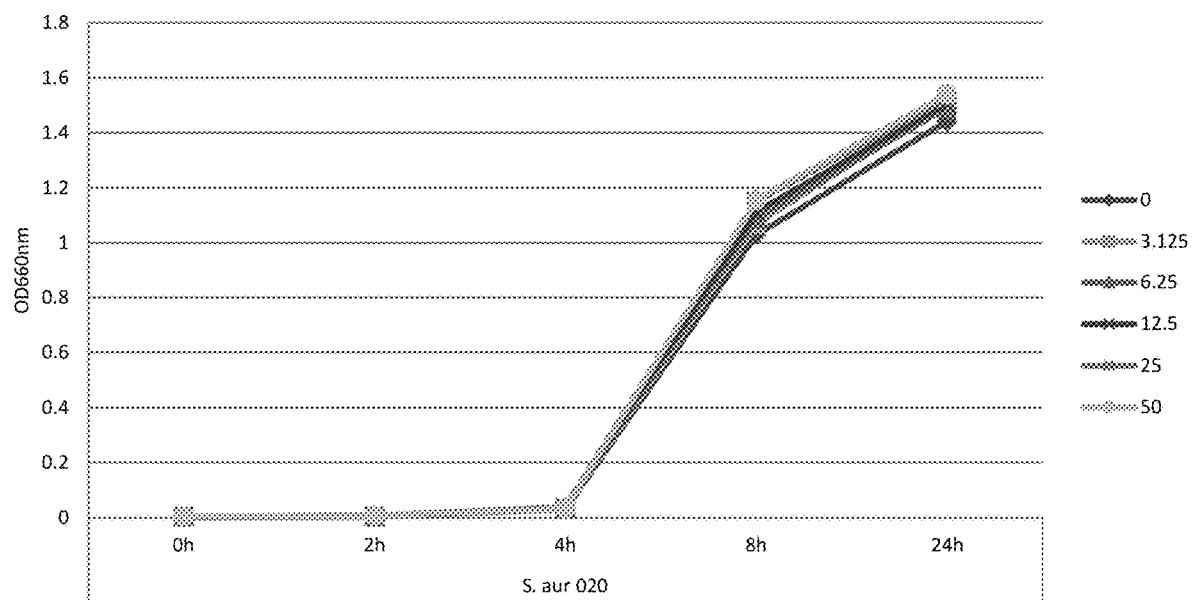
Figure 2E:
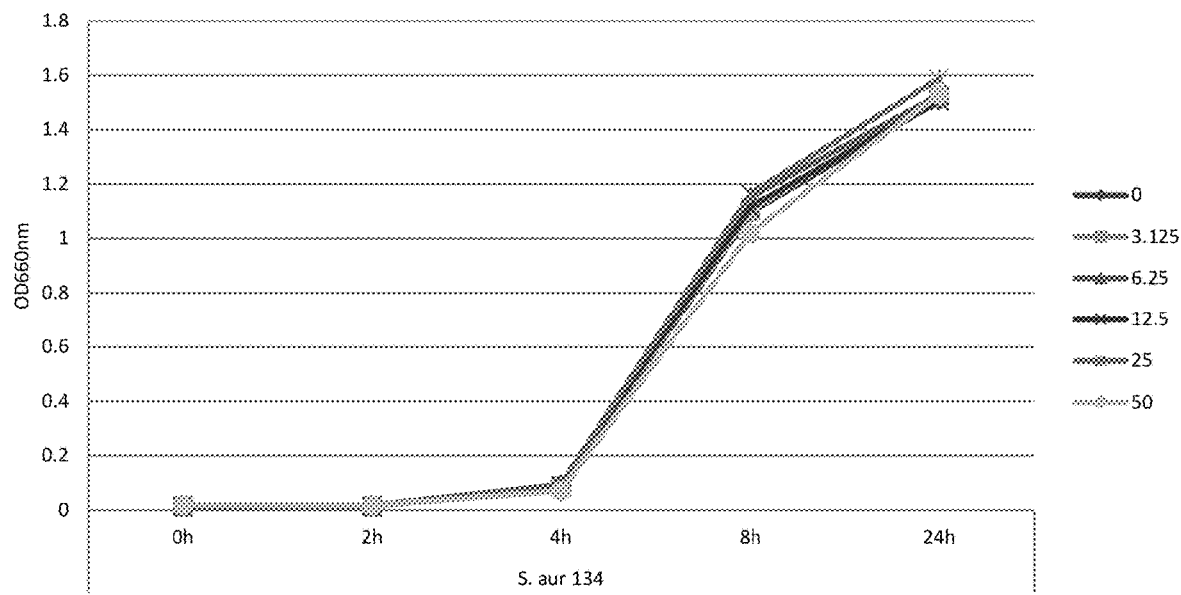
Figure 3A:
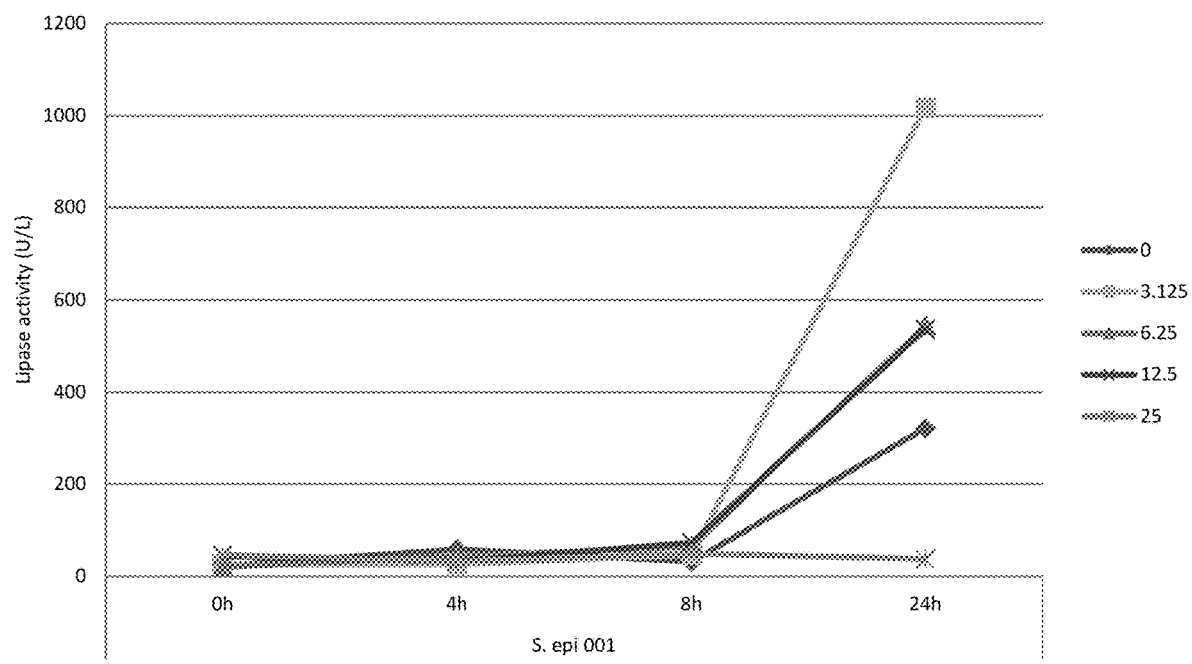
FIGS. 3A, 3B, 3C, 3D, and 3E shows the effect of various µg/ml concentrations of glycerol monolaurate on the lipase activity of several strains of bacteria.
Figure 3B:
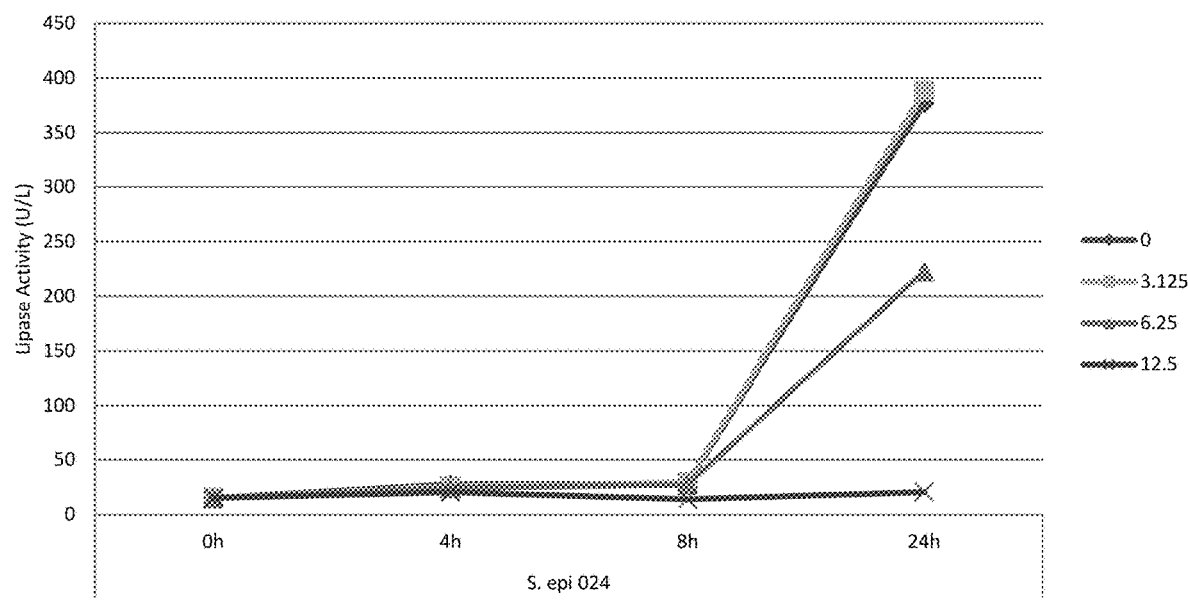
Figure 3C:
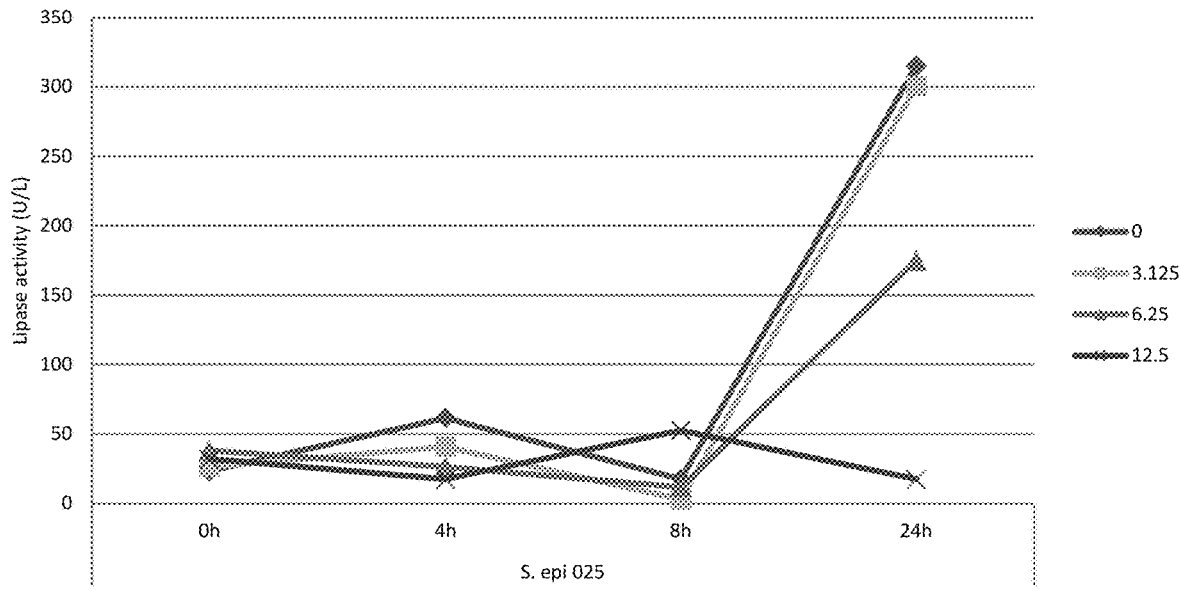
Figure 3D:
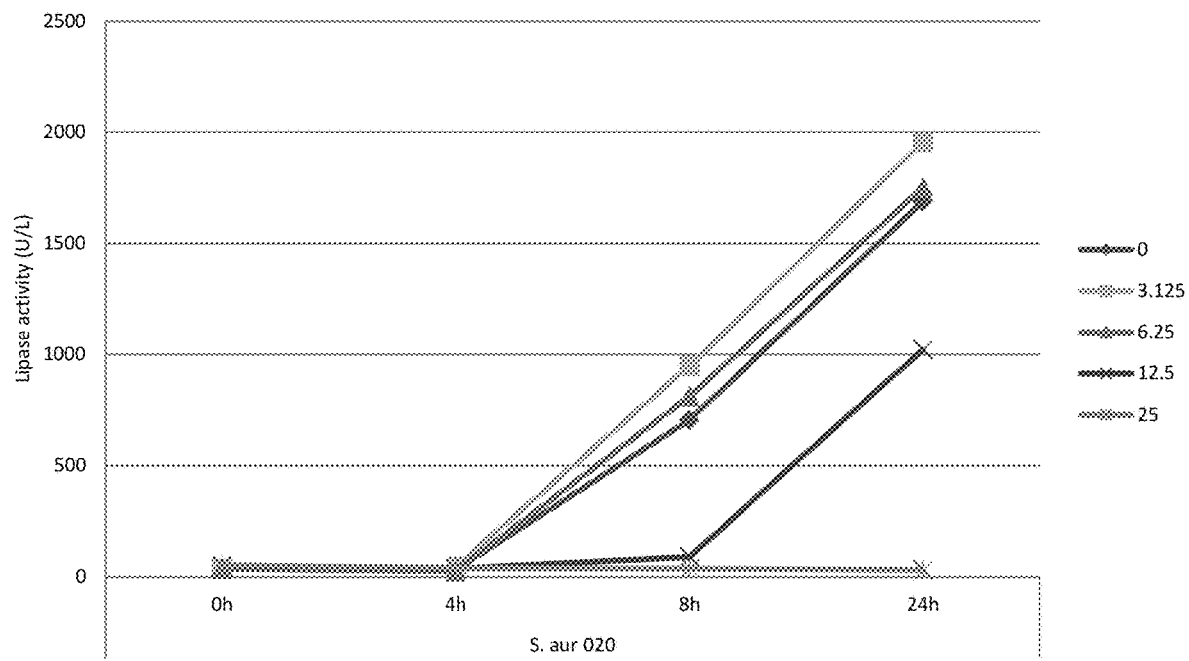
Figure 3E:
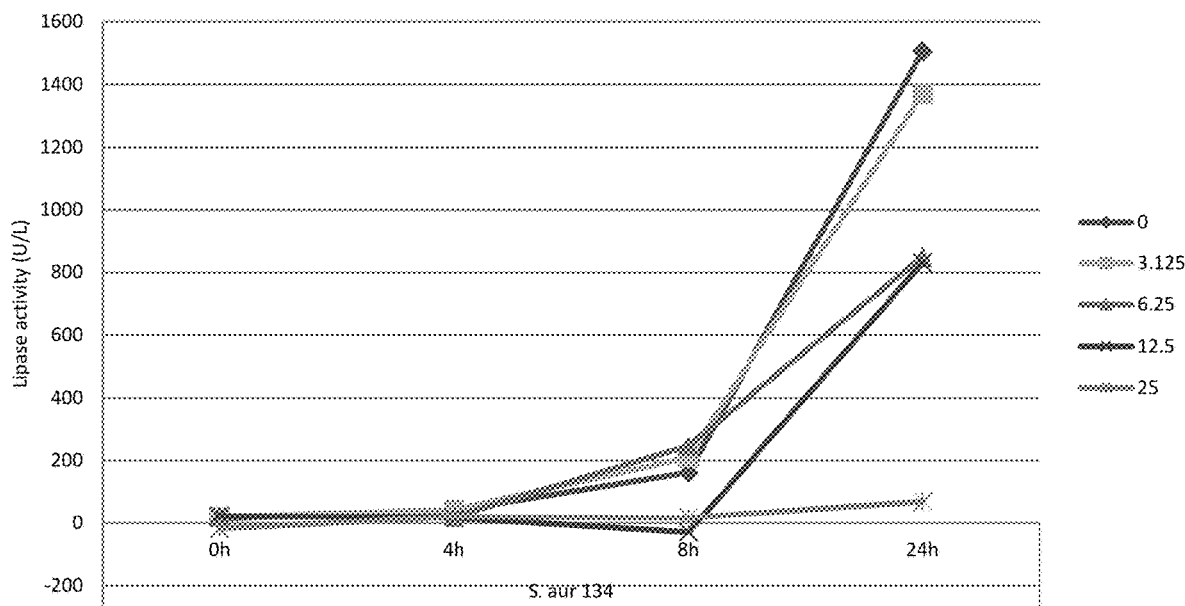
Figure 4A:
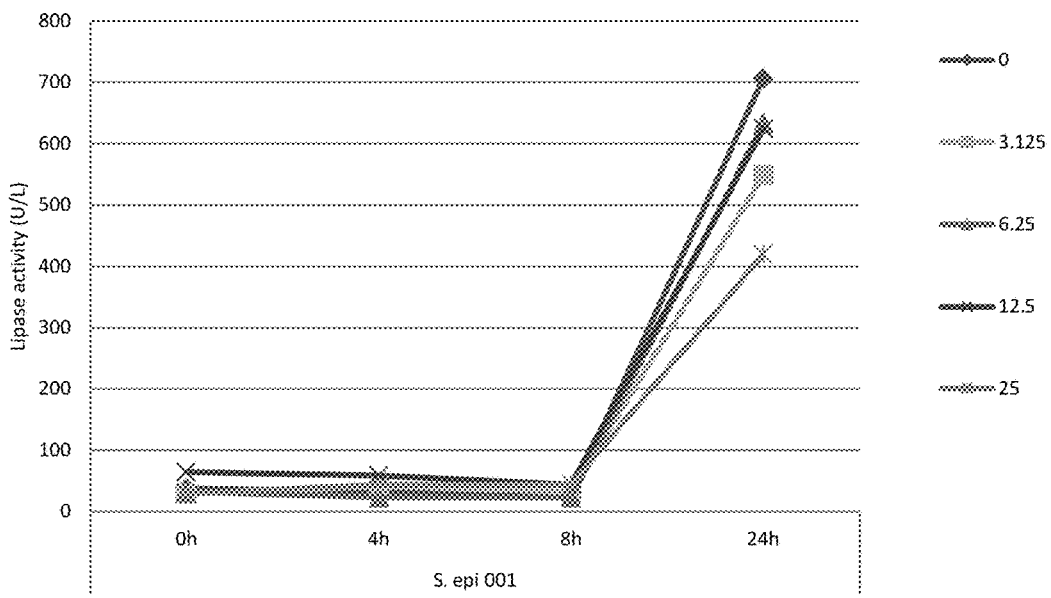
FIGS. 4A, 4B, 4C, 4D, and 4E shows the effect of various µg/ml concentrations of lauric acid on the lipase activity of several strains of bacteria.
Figure 4B:
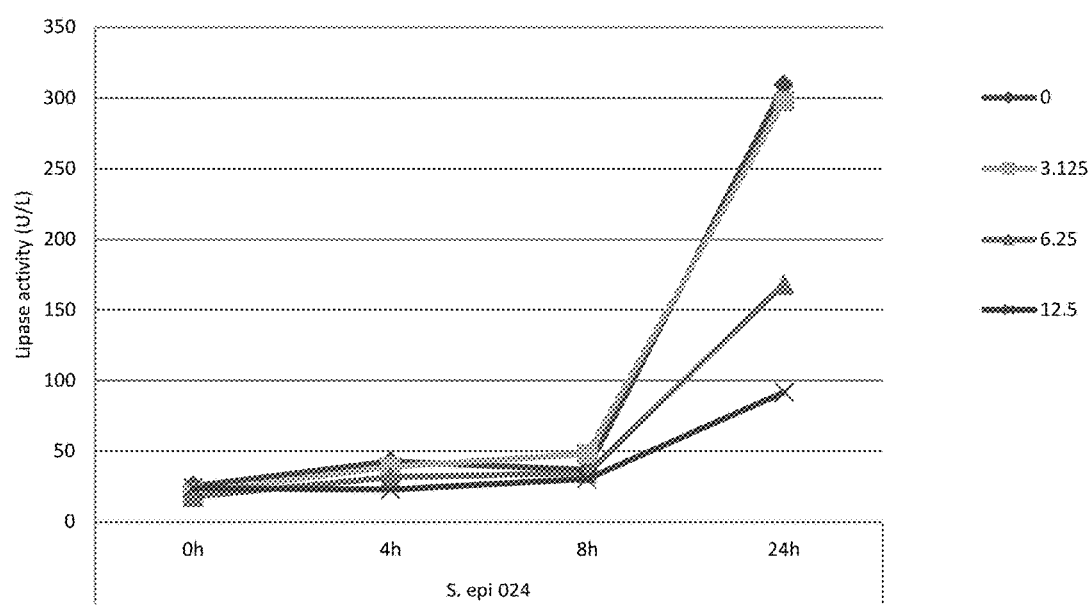
Figure 4C:
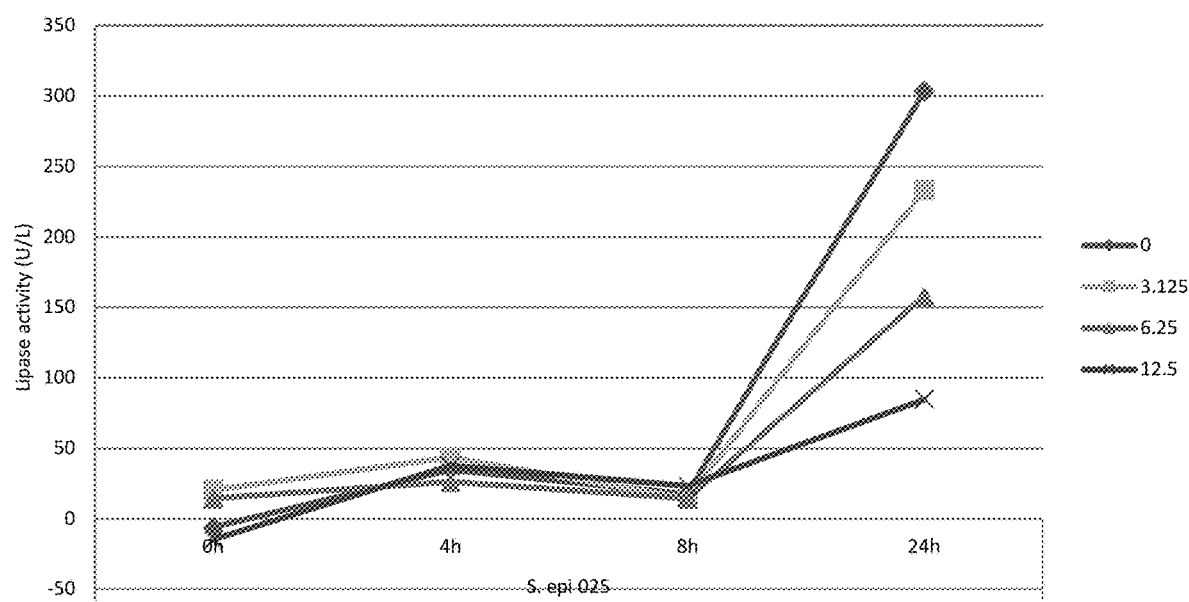
Figure 4D:
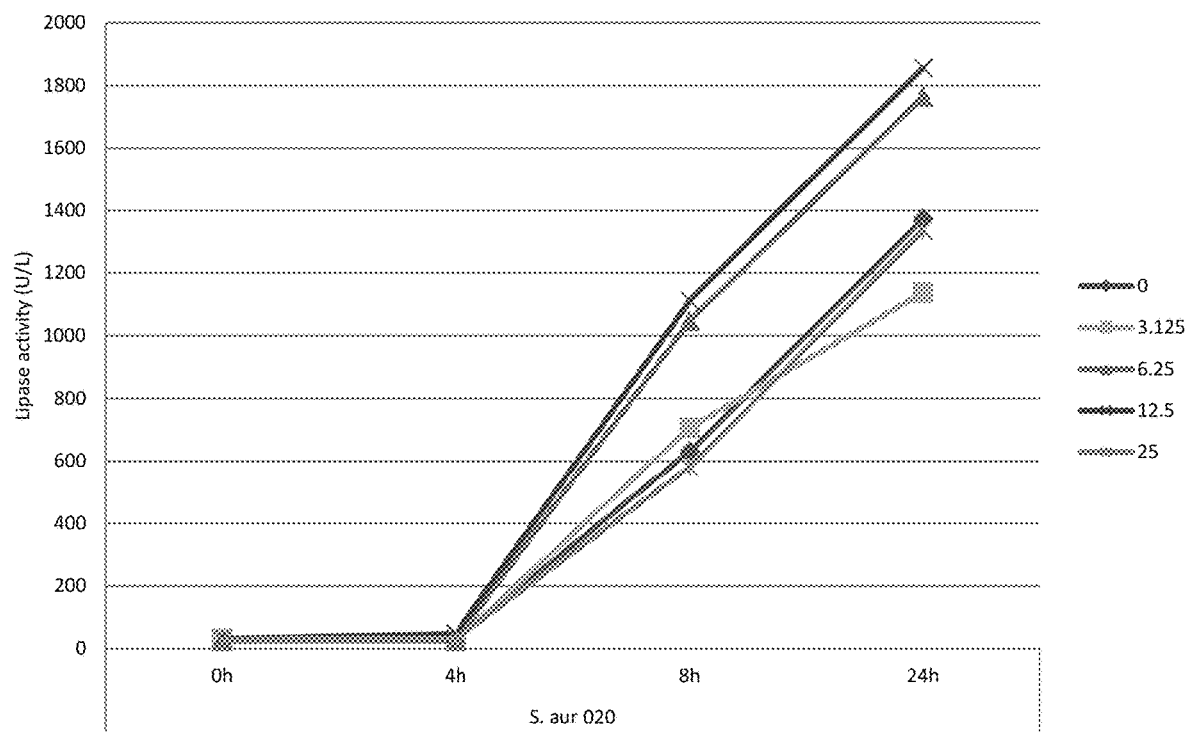
Figure 4E:
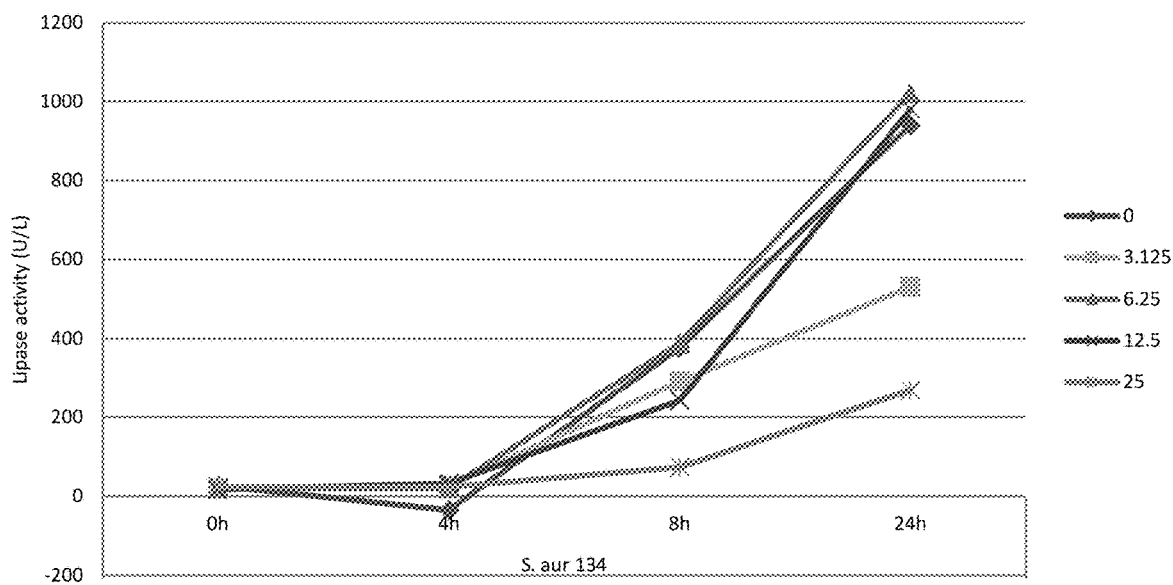

In this example, lipase and bacterial activity has been similarly assayed in five different strains of bacteria (S. epi001, S. epi024, S. epi025, S. aur020 and S. aur134). The bacterial strains were treated with 0, 3.125, 6.25, 12.5 or 25 µg/ml of glycerol monolaurate or lauric acid and grown in TSB at 0.37° C. After incubation for 24 h, both bacterial growth and lipase production were determined. FIG. 1 shows the results of the bacterial growth assay for the strains treated with glycerol monolaurate. FIG. 2 the results of the bacterial growth assay for the strains treated with lauric acid. FIG. 3 shows the results of the lipase production assay for the strains treated with glycerol monolaurate. FIG. 4 shows the results of the lipase production assay for the strains treated with lauric acid. FIG. 5 shows the percentage reduction of lipase production for each test strain and treatment.

Example 3

The following tables provide several examples of compositions, according to certain embodiments. The compositions contain either glycerol monolaurate and/or caprylic acid and/or lauric acid and/or monocaprin with or without androgen, with or without an anti-inflammatory agent, buffer (NaOH/HCl) and a tonicity agent (sodium chloride). Compositions 1, 2 and 4 to 7 contain a preservative (chlorobutanol although benzalkonium chloride or alkyldimethylbenzylammonium chloride could also be used). Composition 3 and 8 is a preservative free preparation containing glycerol monolaurate and composition 9 is a preservative free preparation containing lauric acid. Composition 10 is a preservative free preparation containing glycerol monolaurate and androgen and composition 11 is a preservative free preparation containing lauric acid and androgen. Composition 12 is a preservative free preparation containing glycerol monolaurate and androgen and an anti-inflammatory agent. Composition 13 is a preservative free preparation containing lauric acid and androgen and an antiinflammatory agent. Composition 14 is an ointment formulation with glycerol monolaurate and composition 15 is an ointment formulation with lauric acid. Composition 16 is an ointment formulation with glycerol monolaurate and androgen and composition 17 is an ointment formulation with lauric acid and androgen. Composition 18 is an ointment formulation with glycerol monolaurate and androgen and anti-inflammatory agent and composition 19 is an ointment formulation with lauric acid and androgen and anti-inflammatory agent. Composition 20 is another example of an ointment formulation with glycerol monolaurate and androgen and anti-inflammatory agent. Composition 21 is another example of an ointment formulation with lauric acid and androgen and anti-inflammatory agent. Composition 22 is another example of an ointment formulation with glycerol monolaurate and androgen and anti-inflammatory agent in a different preservative. Composition 23 is another example of an ointment formulation with lauric acid and androgen and anti-inflammatory agent with a different preservative.

Composition 1: Topical Drops Containing Glycerol Monolaurate

| Ingredient | Concentration (wt %) |
|---|---|
| Glycerol monolaurate | 0.005% |
| Androgen | 1% |
| Caprylic capric triglyceride | 5% |
| Chlorobutanol | 0.5% |
| Sorbitan monooleate | 0.5% |
| Potassium dihydrogen orthophosphate ($KH_2PO_4$) | 0.2% |
| di-sodium hydrogen orthophosphate (anhydrous $Na_2HPO_4$) | 1.15% |

| Ingredient | Concentration (wt %) |
| --- | --- |
| Potassium chloride (KCl) | 0.2% |
| Sodium Chloride | 0.8% |
| pH | 6-8 |
| Purified water | Quantity sufficient |

Composition 2: Topical Drops Containing Lauric Acid

| Ingredient | Concentration (wt %) |
| --- | --- |
| Lauric acid | 0.01% |
| Androgen | 1% |
| Caprylic capric triglyceride | 5% |
| Chlorobutanol | 0.5% |
| Sorbitan monooleate | 0.5% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 3: Unit Dose Preservative-Free Preparation

| Ingredient | Concentration (wt %) |
| --- | --- |
| Glycerol monolaurate etc | 0.005% |
| Caprylic capric triglyceride | 5% |
| Sorbitan monooleate | 0.5% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 4: Topical Drops Containing Glycerol Monolaurate

| Ingredient | Concentration (%, w/v) |
| --- | --- |
| Glycerol monolaurate | 0.005% |
| Testosterone | 0.02% |
| Chlorobutanol | 0.3% |
| Sorbitan monooleate | 0.05% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 5: Topical Drops Containing Glycerol Monolaurate and Lauric Acid

| Ingredient | Concentration (%, w/v) |
| --- | --- |
| Glycerol monolaurate | 0.005% |
| Lauric acid | 0.005% |
| Testosterone | 0.02% |
| Chlorobutanol | 0.3% |
| Sorbitan monooleate | 0.05% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 6: Topical Drops Containing Lauric Acid and Monocaprin

| Ingredient | Concentration (%, w/v) |
| --- | --- |
| Lauric acid | 0.005% |
| Monocaprin | 0.005% |
| Testosterone | 0.02% |
| Chlorobutanol | 0.3% |
| Sorbitan monooleate | 0.05% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 7: Topical Drops Containing Lauric Acid

| Ingredient | Concentration (%, w/v) |
| --- | --- |
| Lauric acid | 0.005% |
| Testosterone | 0.02% |
| Chlorobutanol | 0.3% |
| Sorbitan monooleate | 0.05% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 8: Unit Dose Preservative-Free Preparation Containing Glycerol Monolaurate

| Ingredient | Concentration (%, w/v) |
| --- | --- |
| Glycerol monolaurate | 0.005% |
| Caprylic capric triglyceride | 5% |
| Sorbitan monooleate | 0.05% |
| Potassium dihydrogen orthophosphate (KH$_2$PO$_4$) | 0.2% |
| di-sodium hydrogen orthophosphate (anhydrous Na$_2$HPO$_4$) | 1.15% |
| Potassium chloride (KCl) | 0.2% |
| Sodium Chloride | 0.8% |
| pH | 6-8 |
| Purified water | Quantity sufficient |

Composition 9: Unit Dose Preservative-Free Preparation Containing Lauric Acid

| Ingredient | Concentration (%, w/v) |
| --- | --- |
| Lauric acid | 0.005% |
| Caprylic capric triglyceride | 5% |
| Sorbitan monooleate | 0.05% |
| Potassium dihydrogen orthophosphate ($KH_2PO_4$) | 0.2% |
| di-sodium hydrogen orthophosphate (anhydrous $Na_2HPO_4$) | 1.15% |
| Potassium chloride (KCl) | 0.2% |
| Sodium Chloride | 0.8% |
| pH | 6-8 |
| Purified water | Quantity sufficient |

Composition 10: Unit Dose Preservative-Free Preparation Containing Glycerol Monolaurate and Testosterone

| Ingredient | Concentration (%, w/v) |
| --- | --- |
| Glycerol monolaurate | 0.005% |
| Testosterone | 0.02% |
| Caprylic capric triglyceride | 5% |
| Sorbitan monooleate | 0.05% |
| Potassium dihydrogen orthophosphate ($KH_2PO_4$) | 0.2% |
| di-sodium hydrogen orthophosphate (anhydrous $Na_2HPO_4$) | 1.15% |
| Potassium chloride (KCl) | 0.2% |
| Sodium Chloride | 0.8% |
| pH | 6-8 |
| Purified water | Quantity sufficient |

Composition 11: Unit Dose Preservative-Free Preparation Containing Lauric Acid and Testosterone

| Ingredient | Concentration (%, w/v) |
| --- | --- |
| Lauric acid | 0.005% |
| Testosterone | 0.02% |
| Caprylic capric triglyceride | 5% |
| Sorbitan monooleate | 0.05% |
| Potassium dihydrogen orthophosphate ($KH_2PO_4$) | 0.2% |
| di-sodium hydrogen orthophosphate (anhydrous $Na_2HPO_4$) | 1.15% |
| Potassium chloride (KCl) | 0.2% |
| Sodium Chloride | 0.8% |
| pH | 6-8 |
| Purified water | Quantity sufficient |

Composition 12: Unit Dose Preservative-Free Preparation Containing Glycerol Monolaurate, Testosterone, and Anti-Inflammatory Agent

| Ingredient | Concentration (%, w/v) |
| --- | --- |
| Glycerol monolaurate | 0.005% |
| Testosterone | 0.02% |
| alpha-linolenic acid | 0.2% |
| Caprylic capric triglyceride | 5% |
| Sorbitan monooleate | 0.05% |
| Potassium dihydrogen orthophosphate ($KH_2PO_4$) | 0.2% |
| di-sodium hydrogen orthophosphate (anhydrous $Na_2HPO_4$) | 1.15% |
| Potassium chloride (KCl) | 0.2% |
| Sodium Chloride | 0.8% |
| pH | 6-8 |
| Purified water | Quantity sufficient |

Composition 13: Unit Dose Preservative-Free Preparation Containing Lauric Acid, Testosterone, and Anti-Inflammatory Agent

| Ingredient | Concentration (%, w/v) |
| --- | --- |
| Lauric acid | 0.005% |
| Testosterone | 0.02% |
| alpha-linolenic acid (Omega 3 fatty acids) | 0.2% |
| Caprylic capric triglyceride | 5% |
| Sorbitan monooleate | 0.05% |
| Potassium dihydrogen orthophosphate ($KH_2PO_4$) | 0.2% |
| di-sodium hydrogen orthophosphate (anhydrous $Na_2HPO_4$) | 1.15% |
| Potassium chloride (KCl) | 0.2% |
| Sodium Chloride | 0.8% |
| pH | 6-8 |
| Purified water | Quantity sufficient |

Composition 14: Topical Ointment Containing Glycerol Monolaurate

| Ingredient | Concentration (%, w/w) |
| --- | --- |
| Glycerol monolaurate | 0.05% |
| Sorbitan monooleate | 0.05% |
| Butylated Hydroxytoluene | 0.03% |
| Olive oil | 30% |
| Ophthalmic ointment base (lanolin anhydrous 10%, mineral oil light 10%, petroleum white 80%) | Quantity sufficient |

Composition 15: Topical Ointment Containing Lauric Acid

| Ingredient | Concentration (%, w/w) |
| --- | --- |
| Lauric acid | 0.05% |
| Sorbitan monooleate | 0.05% |
| Butylated Hydroxytoluene | 0.03% |
| Olive oil | 30% |
| Ophthalmic ointment base (lanolin anhydrous 10%, mineral oil light 10%, petroleum white 80%) | Quantity sufficient |

Composition 16: Topical Ointment Containing Glycerol Monolaurate and Testosterone

| Ingredient | Concentration (%, w/w) |
| --- | --- |
| Glycerol monolaurate | 0.05% |
| Testosterone | 0.02% |
| Sorbitan monooleate | 0.05% |
| Butylated Hydroxytoluene | 0.03% |
| Olive oil | 30% |
| Ophthalmic ointment base (lanolin anhydrous 10%, mineral oil light 10%, petroleum white 80%) | Quantity sufficient |

Composition 17: Topical Ointment Containing Lauric Acid and Testosterone

| Ingredient | Concentration (%, w/w) |
| --- | --- |
| Lauric acid | 0.05% |
| Testosterone | 0.02% |
| Sorbitan monooleate | 0.05% |
| Butylated Hydroxytolune | 0.03% |
| Olive oil | 30% |
| Ophthalmic ointment base (lanolin anhydrous 10%, mineral oil light 10%, petroleum white 80%) | Quantity sufficient |

Composition 18: Topical Ointment Containing Glycerol Monolaurate, Testosterone and Anti-Inflammatory Agent

| Ingredient | Concentration (%, w/w) |
| --- | --- |
| Glycerol monolaurate | 0.05% |
| Testosterone | 0.02% |
| alpha-linolenic acid | 0.2% |
| Sorbitan monooleate | 0.05% |
| Butylated Hydroxytolune | 0.03% |
| Olive oil | 30% |
| Ophthalmic ointment base (lanolin anhydrous 10%, mineral oil light 10%, petroleum white 80%) | Quantity sufficient |

Composition 19: Topical Ointment Containing Lauric Acid, Testosterone and Anti-Inflammatory Agent

| Ingredient | Concentration (%, w/w) |
| --- | --- |
| Lauric acid | 0.05% |
| Testosterone | 0.02% |
| alpha-linolenic acid | 0.2% |
| Sorbitan monooleate | 0.05% |
| Butylated Hydroxytolune | 0.03% |
| Olive oil | 30% |
| Ophthalmic ointment base (lanolin anhydrous 10%, mineral oil light 10%, petroleum white 80%) | Quantity sufficient |

Composition 20: Topical Ointment Containing Glycerol Monolaurate

| Ingredient | Concentration (%, w/w) |
| --- | --- |
| Glycerol monolaurate | 0.05% |
| Testosterone | 0.02% |
| alpha-linolenic acid | 0.2% |
| Vit E | 2.5% |
| Olive oil | 30% |
| Ophthalmic ointment base (lanolin anhydrous 10%, mineral oil light 10%, petroleum white 80%) | Quantity sufficient |

Composition 21: Topical Ointment Containing Lauric Acid

| Ingredient | Concentration (%, w/w) |
| --- | --- |
| Lauric acid | 0.05% |
| Testosterone | 0.02% |
| alpha-linolenic acid | 0.2% |
| Vit E | 2.5% |
| Olive oil | 30% |
| Ophthalmic ointment base (lanolin anhydrous 10%, mineral oil light 10%, petroleum white 80%) | Quantity sufficient |

Composition 22: Topical Ointment Containing Glycerol Monolaurate

| Ingredient | Concentration (%, w/w) |
| --- | --- |
| Glycerol monolaurate | 0.05% |
| Testosterone | 0.02% |
| alpha-linolenic acid | 0.2% |
| Vit E | 1% |
| Caprylic capric triglyceride | 5% |
| Olive oil | 25% |
| Ophthalmic ointment base (lanolin anhydrous 10%, mineral oil light 10%, petroleum white 80%) | Quantity sufficient |

Composition 23: Topical Ointment Containing Lauric Acid

| Ingredient | Concentration (%, w/w) |
| --- | --- |
| Lauric acid | 0.05% |
| Testosterone | 0.02% |
| alpha-linolenic acid | 0.2% |
| Vit E | 1% |
| Caprylic capric triglyceride | 5% |
| Olive oil | 25% |
| Ophthalmic ointment base (lanolin anhydrous 10%, mineral oil light 10%, petroleum white 80%) | Quantity sufficient |

Other exemplary non-limiting embodiments are described in the numbered paragraphs below. Any reference to a numbered paragraph is reference to a paragraph within this section.

1. A method for treating a dry eye disorder in a subject by administering an amount of one or more fatty acids and/or fatty acid esters therapeutically effective to inhibit lipase activity without substantially altering the dynamic microbial community of the eye.
2. The method of paragraph 1 wherein the fatty acids and/or fatty acid esters are $C_8$ to $C_{16}$ fatty acids and/or fatty acid esters.
3. The method of paragraph 1 wherein the fatty acids and/or fatty acid esters are $C_{10}$ to $C_{14}$ fatty acids and/or fatty acid esters
4. The method of one or more of the proceeding paragraphs, wherein the fatty acids and/or fatty acid esters are one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or combinations thereof.
5. The method of one or more of the proceeding paragraphs, wherein the fatty acid and/or fatty acid ester is glycerol monolaurate, lauric acid or a combination thereof.
6. The method of one or more of the preceding paragraphs further comprising administering a therapeutically effective amount of androgen.
7. The method of paragraph 6, wherein the androgen is selected from one or more of the following: dehydroepiandrosterone (DHEA), androsterone, testosterone and dihydrotestosterone.

8. The method of one of or more of the preceding paragraphs further comprising administering a therapeutically effective amount of an anti-inflammatory agent.
9. The method of paragraph 8, wherein the anti-inflammatory agent is selected from one or more of the following: azithromycin, cyclosporine A, omega-3 fatty acids and transforming growth factor beta (TGF-β).
10. The method of one of or more of the preceding paragraphs wherein the administration is topically to the eye.
11. The method of one of or more of the preceding paragraphs wherein the concentration of fatty acids and/or fatty acid esters is about 0.01 to 50 µg/ml in the eye drops or associated with the contact lens.
12. The method of one of or more of the preceding paragraphs wherein the concentration of fatty acids and/or fatty acid esters is about 0.00001% to 0.005% by weight of the total volume of the eye drops.
13. The method of paragraph 10, wherein the topical administration is in the form of an ointment, cream, eye drops or released from an ophthalmic device.
14. The method of paragraph 12, wherein the ophthalmic device is a contact lens.
15. The method of one or more of the proceeding paragraphs, wherein the amount of glycerol monolaurate included in the eye drops or associated with the contact lenses is in a concentration of about 0.01 to 50 µg/ml.
16. The method of one or more of proceeding paragraphs, wherein the amount of lauric acid included in the eye drops or associated with the contact lenses is in a concentration of about 0.01 to 50 µg/ml.
17. The method of one or more of proceeding paragraphs, wherein the amount of the fatty acids and/or fatty acid eaters included in the ointment or the cream is in a concentration of about 0.005% to 0.05% weight of the total weight of the ointment or the cream.
18. The method of one or more of the proceeding paragraphs, wherein the amount of glycerol monolaurate included in the ointment or the cream is in a concentration of about 0.005% to 0.05% by weight of the total weight of the ointment or the cream.
19. The method of one or more of the proceeding paragraphs, wherein the amount of lauric acid included in the eye drops or associated with the contact lenses is in a concentration of about 2.5 to about 25 µg/ml.
20. The methods of one or more of the proceeding paragraphs, wherein the administration is oral.
21. The method of one or more of the preceding paragraphs wherein the administration is to alleviate symptoms of a dry eye or for preventing the dry eye disorder in the subject.
22. A composition for treating a dry eye disorder in a subject, wherein the composition comprises an amount of one or more fatty acids and/or fatty acid esters therapeutically effective to inhibit lipase activity without substantially altering the dynamic microbial community of the eye.
23. A composition for treating a dry eye disorder in a subject, the composition comprising a therapeutically effective amount of: one or more fatty acids and/or fatty acid esters and an androgen, wherein the composition is effective to inhibit lipase activity without substantially altering the dynamic microbial community of the eye.
24. A composition for treating a dry eye disorder in a subject, the composition comprising a therapeutically effective amount of: one or more fatty acids and/or fatty acid esters; an androgen and an anti-inflammatory agent, wherein the composition is effective to inhibit lipase activity without substantially altering the dynamic microbial community of the eye.
25. A composition for treating a dry eye disorder in a subject, the composition comprising a therapeutically effective amount of: one or more fatty acids and/or fatty acid esters and an anti-inflammatory agent, wherein the composition is effective to inhibit lipase activity without substantially altering the dynamic microbial community of the eye.
26. A composition for treating a dry eye disorder in a subject, the composition comprising: one or more fatty acids and/or fatty acid esters and the concentration of one or more fatty acids and/or fatty acid esters in the composition is about 0.01 to about 50 µg/ml; and an amount of androgen that is about 0.05% to about 3% by weight of the total weight of the composition, wherein the composition is effective to inhibit lipase activity without substantially altering the dynamic microbial community of the eye.
27. A composition for treating a dry eye disorder in a subject, the composition comprising: one or more fatty acids and/or fatty acid esters and the concentration of one or more fatty acids and/or fatty acid esters in the composition is about 2.5 to about 25 µg/ml; an amount of androgen that is about 0.05% to about 3% by weight of the total weight of the composition and an anti-inflammatory agent that is about 0.001% to about 5% by weight of the total weight of the composition, wherein the composition is effective to inhibit lipase activity without substantially altering the dynamic microbial community of the eye.
28. A composition for treating a dry eye disorder in a subject, the composition comprising: one or more fatty acids and/or fatty acid esters and the concentration of one or more fatty acids and/or fatty acid esters in the composition is about 2.5 to about 25 µg/ml and an anti-inflammatory agent that is about 0.001% to about 5% by weight of the total weight of the composition, wherein the composition is effective to inhibit lipase activity without substantially altering the dynamic microbial community of the eye.
29. A cream or ointment composition for treating a dry eye disorder in a subject, the composition comprising: one or more fatty adds and/or fatty acid esters that is about 0.005% to about 0.05% by weight of the total weight of the composition; and an amount of androgen that is about 0.05% to about 3% by weight of the total weight of the composition, wherein the composition is effective to inhibit lipase activity without substantially altering the dynamic microbial community of the eye.
30. A composition for treating a dry eye disorder in a subject, the composition comprising: one or more fatty acids and/or fatty acid esters and that is about 0.005% to about 0.05% by weight of the total weight of the composition; an amount of androgen that is about 0.05% to about 3% by weight of the total weight of the composition and an anti-inflammatory agent that is about 0.001% to about 5% by weight of the total weight of the composition, wherein the composition is effective to inhibit lipase activity without substantially altering the dynamic microbial community of the eye.

31. A composition for treating a dry eye disorder in a subject, the composition comprising: one or more fatty acids and/or fatty acid esters that is about 0.005% to about 0.05% by weight of the total weight of the composition; and an anti-inflammatory agent that is about 0.001% to about 5% by weight of the total weight of the composition, wherein the composition is effective to inhibit lipase activity without substantially altering the dynamic microbial community of the eye.

32. A composition according to one or more of the proceeding paragraphs further comprises a therapeutically effective amount of androgen.

33. A composition according to paragraph 32 wherein the androgen is selected from one or more of the following: dehydroepiandrosterone (DHEA), androsterone, testosterone and dihydrotestosterone.

34. A composition according to one or more of the proceeding paragraphs further comprises a therapeutically effective amount of an anti-inflammatory agent.

35. A composition according to paragraph 34 wherein the anti-inflammatory agent is selected from one or more of the following: azithromycin, cyclosporine A, omega-3 fatty acids and transforming growth factor beta (TGF-β).

36. A composition according to one or more of the proceeding paragraphs, wherein the composition is suitable for topical administration to an eye.

37. The composition of one of or more of the preceding paragraphs wherein the concentration of fatty acids and/or fatty acid esters is about 0.01 to 50 μg/ml in the eye drops or associated with the contact lens.

38. A composition according to one or more of the proceeding paragraphs, wherein the fatty acids and/or fatty acid esters are $C_8$ to $C_{16}$ fatty acids and/or fatty acid esters.

39. A composition according to one or more of the proceeding paragraphs, wherein the fatty acids and/or fatty acid esters are $C_{10}$ to $C_{14}$ fatty acids and/or fatty acid esters.

40. The composition of one or more of the proceeding paragraphs, wherein the fatty acids and/or fatty acid esters are one or more of the following fatty acids and/or fatty acid esters: $C_8$, $C_{10}$, $C_{11}$, $C_{12}$, $C_{14}$, glycerol monolaurate, lauric acid, capric acid, caprylic acid, myristic acid or combinations thereof.

41. A composition according to one or more of the proceeding paragraphs, wherein the fatty acid and/or related fatty acid ester is glycerol monolaurate, lauric acid or a combination thereof.

42. A composition according to one or more of the proceeding paragraphs further comprises a therapeutically effective amount of androgen.

43. A composition according to paragraph 42 wherein the androgen is selected from one or more of the following: dehydroepiandrosterone (DHEA), androsterone, testosterone and dihydrotestosterone.

44. A composition according to one or more of the proceeding paragraphs further comprises a therapeutically effective amount of an anti-inflammatory agent.

45. A composition according to paragraph 44 wherein the anti-inflammatory agent is selected from one or more of the following: azithromycin, cyclosporine A, omega-3 fatty acids and transforming growth factor beta (TGF-β).

46. A composition according to one or more of the proceeding paragraphs, wherein the composition is suitable for topical administration to an eye.

47. The composition of one of or more of the preceding paragraphs wherein the concentration of fatty acids and/or fatty acid esters is about 0.01 to 50 μg/ml in the eye drops or associated with the contact lens.

48. The composition of one of or more of the preceding paragraphs wherein the concentration of fatty acids and/or fatty acid esters is about 0.00001% to 0.005% by weight of the total volume of the eye drops.

49. A composition according to paragraph 46 wherein the topical administration is in the form of an ointment, cream, eye drops or released from an ophthalmic device.

50. A composition according to paragraph 49 wherein the ophthalmic device is a contact lens.

51. A composition according to one or more of the above composition paragraphs, wherein the amount of glycerol monolaurate included in eye drops or associate with the contact lenses is in a concentration of about 0.01 to 50 μg/ml.

52. A composition according to one or more of the proceeding paragraphs, wherein the amount of lauric acid included in eye drops or associated with the contact lenses is in a concentration of about 0.01 to 50 μg/ml.

53. A composition according to one or more of proceeding paragraphs, wherein the amount of the fatty acids and/or fatty acid esters included in the ointment or the cream is in a concentration of about 0.005% to 0.05% weight of the total weight of the ointment or the cream.

54. A composition according to one or more of the above composition claims, wherein the composition is suitable for oral administration.

55. A composition for use in a method of treating a dry eye disorder wherein the method comprises administering the composition to a subject, wherein the composition comprises an amount of one or more fatty acids or fatty acid esters therapeutically effective to inhibit lipase activity without substantially altering the dynamic microbial community of the eye.

56. The composition for use in the method of one or more of the preceding claims, wherein the method further comprises administering a therapeutically effective amount of androgen and/or a therapeutically effective amount of an anti-inflammatory agent.

57. The composition for use in the method of one or more of the preceding claims wherein the eye disorder is dry eye.

58. The composition for use in the method of one or more of the preceding claims wherein the method comprises administering the glycerol monolaurate and lauric acid in the form of eye drops or released from a contact lens.

Additionally, the disclosure has been described with reference to particular embodiments. However, it may be readily apparent to those skilled in the art that it is possible to embody the disclosure in specific forms other than those of the embodiments described above. The embodiments are merely illustrative and should not be considered restrictive.

The invention claimed is:

1. A composition for treating a dry eye disorder in a subject, comprising: an amount of lauric acid or a combination of lauric acid and glycerol monolaurate therapeutically effective to inhibit lipase activity by about 35% to 75% in an eye of the subject without substantially altering the dynamic microbial community of the eye to which the composition has been administered;

wherein the amount of lauric acid or a combination of lauric acid and glycerol monolaurate is in a concentration of between 2.5 µg/ml to 15 µg/ml in the composition.

2. A composition according to claim 1 further comprises a therapeutically effective amount of androgen or androgen analogue.

3. A composition according to claim 2 wherein the androgen and/or androgen analogue is selected from one or more of the following: dehydroepiandrosterone (DHEA), androsterone, testosterone and dihydrotestosterone.

4. A composition according to claim 1 further comprises a therapeutically effective amount of an anti-inflammatory agent.

5. A composition according to claim 4 wherein the anti-inflammatory agent is selected from one or more of the following: azithromycin, cyclosporine A, omega-3 fatty acids and transforming growth factor beta (TGF-β).

6. A composition according to claim 1, wherein the composition is suitable for topical administration to an eye.

7. A composition according to claim 6, wherein the topical administration is in the form of an ointment, cream, eye drops or released from an ophthalmic device.

8. A composition according to claim 7, wherein the ophthalmic device is a contact lens.

9. The composition of claim 7, wherein the concentration of fatty acids and/or fatty acid esters is about 0.01 to 50 µg/ml in the eye drops.

10. The composition of claim 7 wherein the concentration of lauric acid or a combination of lauric acid and glycerol monolaurate is between 2.5 µg/ml to 15 µg/ml in the composition associated with the contact lens.

11. The composition of claim 7 wherein the concentration of lauric acid or a combination of lauric acid and glycerol monolaurate is about 0.00001% to 0.005% % by weight of the total volume of the eye drops.

12. A composition according to claim 7, wherein the amount of the lauric acid or a combination of lauric acid and glycerol monolaurate included in the ointment or the cream is in a concentration of about 0.005% to 0.05% weight of the total weight of the ointment or the cream.

13. A composition according to claim 7, wherein the amount of lauric acid or a combination of lauric acid and glycerol monolaurate included in the eye drops is in a concentration of between 2.5 µg/ml to 15 µg/ml.

14. A composition according to claim 1, wherein the composition comprises an amount of lauric acid or a combination of lauric acid and glycerol monolaurate therapeutically effective to inhibit lipase activity in an eye of the subject while permitting bacterial growth.

* * * * *